under the patent number US 6,878,528 B1.

(12) United States Patent
Duvert-Frances et al.

(10) Patent No.: US 6,878,528 B1
(45) Date of Patent: Apr. 12, 2005

(54) POLYNUCLEOTIDES ENCODING A MAMMALIAN LANGERHANS CELL ANTIGEN

(75) Inventors: Valerie Duvert-Frances, Tasin la Demi-Lune (FR); Jean-Jacques Pin, Saint Bonnet de Mure (FR); Jenny Valladeau, Lyons (FR); Valerie Clair, Lyons (FR); Sem Saeland, Lyons (FR); Serge J. E. Lebecque, Civrieux d'Azergues (FR)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/787,192

(22) PCT Filed: Sep. 23, 1999

(86) PCT No.: PCT/US99/22269

§ 371 (c)(1),
(2), (4) Date: Mar. 15, 2001

(87) PCT Pub. No.: WO00/18803

PCT Pub. Date: Apr. 6, 2000

(30) Foreign Application Priority Data

Sep. 25, 1998 (EP) ............................................. 98402374
Feb. 18, 1999 (EP) ............................................. 98400394

(51) Int. Cl.[7] .................................................. C12P 21/06
(52) U.S. Cl. .................... 435/69.1; 536/23.1; 536/23.5; 435/320.1; 435/252.3
(58) Field of Search .............................. 536/23.1, 23.5; 435/69.1, 252.3, 320.1

(56) References Cited

U.S. PATENT DOCUMENTS 5,861,244 A * 1/1999 Wang et al.

OTHER PUBLICATIONS

Hu et al. J Bacteriol 174(8):2679, 1992.*
Sequence Search Listings pp. 10–12, 38–39, 1998.*
Martin et al. Accession No. L81685 GenEmbl, 1997.*
Valladeau et al., 1997, Abstract and oral presentation at 5th International Workshop on Langerhans Cells, *The Journal of Investigative Dermatology*, 109(2):267.
Valladeau et al., 1999, *Eur. J. Immunology*, 29:2695–2704.

* cited by examiner

*Primary Examiner*—G. R. Ewoldt
(74) *Attorney, Agent, or Firm*—Michael G. Biro; Immac Thampoe

(57) ABSTRACT

Purified mammalian DC cell surface protein, designated Langerin, nucleic acids encoding Langerin, and antibodies which specifically bind Langerin.

6 Claims, No Drawings

US 6,878,528 B1

POLYNUCLEOTIDES ENCODING A MAMMALIAN LANGERHANS CELL ANTIGEN

The present application is a 35 U.S.C. 371 National Phase application of PCT/US99/22269, filed Sep. 23, 1999, which claims priority from European Application Number 98 402 374.7, filed Sep. 25, 1998, and European Application Number 99 400 394.5, filed Feb. 18, 1999.

FIELD OF THE INVENTION

The present invention relates to compositions which function in controlling physiology, development, and differentiation of mammalian cells, e.g., cells of a mammalian immune system. In particular, it provides antibodies, e.g., agonists and antagonists, which regulate cellular physiology, development, differentiation, or function of various cell types, including hematopoietic cells, and particularly dendritic cells e.g., Langerhans cells.

BACKGROUND OF THE INVENTION

Dendritic cells (DC) are antigen-presenting cells that are required for initiation of a specific immune response. See, e.g., Banchereau and Steinman (1998) *Nature* 392:242–52. One type of DC is exemplified by Langerhans cells (LC), immature DC cells that reside in non-lymphoid tissue, such as the epidermis, and whose primary function is to capture antigen. See, e.g., Steinman, et al. (1995) *J. Exp. Med.* 182:283–288.

Antigen capture is achieved primarily through specialized surface-membrane endocytic structures or through macropinocytosis, thus permitting Langerhans cells to concentrate solutes which are present in large volumes of fluid. See, e.g., Sallusto, et al. (1995) *J. Exp. Med.* 182:389–400. Concomitant with processing of antigen in specialized organelles of the endocytic pathway, DC, such as Langerhans cells, migrate to secondary lymphoid tissue and undergo a number of phenotypic modifications. These maturation events ultimately translate into highly efficient presentation of processed antigen, by appropriate MHC molecules of the DC, to T cells.

In particular, the maturation process of the DC Langerhans cell includes loss of adhesion receptors such as E-cadherin, and the disappearance of Birbeck granules (BG), which are characteristic for LC. Conversely, upon acquisition of antigen-presentation function, costimulatory receptors such as the CD80 and CD86 molecules are upregulated on DC to permit T cell activation. Maturation events of DC can be reconstituted in vitro by TNF-α and CD40-ligand which mimic, respectively, the response to pro-inflammatory cytokines following encounter with pathogen, and the response to contact with T cells in secondary lymphoid tissue. See, e.g., Caux, et al. (1996) *J. Exp. Med.* 184:695–706.

Thus, it is apparent that the highly specialized and anatomically localized functions of DC are controlled by tight regulation of the expression of a number of key molecules.

Recently, culture systems have become available to obtain large numbers of DC when cultured in the presence of cytokines. Using such culture methods, DC can be obtained for in vitro study from CD34+ hematopoietic progenitor cells (HPC) present in cord blood when the HPC are co-cultured with TNF-α and GM-CSF (such cultures are referred to as CD34-derived DC), or from peripheral blood monocytes when they are co-cultured with GM-CSF and IL-4 (such cultures are referred to as monocyte-derived DC). See, e.g., Caux, et al. (1992) *Nature* 392:258–261; Chapuis, et al. (1997) *Eur. J. Immunol.* 27:431–441; Romani, et al. (1994) *J. Invest. Dermatol.* 93:600–609.

These methods permit either, the in vitro (see, e.g., Caux, et al. (1996) *J. Exp. Med.* 184:695–706), or, the ex-vivo (from various organs; see e.g., Grouard, et al. (1996) *Nature* 384:364–367; O'Doherty, et al. (1994) *Immunol.* 82:487–493; Zhou (1995) *J. Immunol.* 154:3821–3835) isolation of phenotypically and functionally distinct DC subpopulations.

Consequently, it would be of great benefit to possess novel reagents capable of identifying markers that are expressed and associated with different DC subpopulations. These markers are detectable using antibodies, e.g., monoclonal or polyclonal. Such markers would permit the monitoring, characterization, and/or isolation of defined subsets of immature DCs by facilitating, e.g., cell-sorting and functional studies. Thus, needs exist for tools which permit a better understanding of the molecules involved in DC maturation, antigen presentation, and the mechanisms of DC interaction with other molecules, cells, and tissues. The present invention fulfills such needs by providing useful reagents and compositions involved in DC maturation and function.

SUMMARY OF THE INVENTION

The present invention is based, in part, upon the discovery of an antibody which defines and recognizes a novel cell antigen found on dendritic cells (DC) and Langerhans cells (LC). This monoclonal antibody is designated DCGM4 and the antigen it recognizes has been designated Langerin. The invention embraces this antibody and methods for its use. In addition, the invention is directed to antigen recognized by this antibody, along with variants of these proteins, e.g., mutations (muteins) of the natural sequence, species and allelic variants, fusion proteins, chemical mimetics, and other structural or functional analogs. Various uses of these different antibodies and protein compositions are also provided.

The present invention provides antibody which binds specifically to a mammalian Langerin. In preferred embodiments the mammal is a primate; or the antibodies are a monoclonal antibody, interfere with binding of DCGM4 to the Langerin, or are detectably labeled, e.g., with a fluorescent or enzymatic label.

The invention also provides methods of detecting a mammalian Langerin, comprising binding DCGM4 to Langerin. In various embodiments, the antibody is a labeled antibody or is immobilized to a solid substrate; the Langerin is expressed on a cell surface; the detecting allows isolation of a cell which comprises a nucleic acid which expresses Langerin; or the detecting further allows purification of Langerin. The invention also embraces a kit for detecting Langerin with a compartment containing an antibody. In preferred embodiments, the kit is a fluorescence immunoassay kit.

The present invention further provides methods of modulating an immune function modulated by a cell comprising contacting said cell with an antibody described herein. For instance, the modulation can be blocking DC cell maturation or function.

Also embraced herein are methods for analyzing a DC cell population, comprising measuring the presence of Langerin. Typically, the measuring is a quantitative determination, e.g., by measuring binding of an antibody to Langerin.

The invention also provides substantially pure mammalian Langerin antigens. Human Langerin and mouse Langerin are specifically described. Langerin can be purified by, for example, immunoaffinity, e.g., using an antibody which binds specifically to a mammalian Langerin. A preferred antibody for such is DCGM4. Along with full length Langerin, the invention provides fragments which express an immunological epitope of said Langerin or modulate an immune response, e.g., a response mediated by a DC cell, including a Langerin+ cell.

The invention further provides genomic DNA of human langerin.

DETAILED DESCRIPTION OF THE INVENTION

All publications, patent applications, patents, and other references mentioned herein are incorporated by reference in their entirety including all figures, graphs, and drawings.
General The present invention provides antibodies which recognize a mammalian protein that exhibits properties characteristic of functionally significant DC expressed molecules. The antibody is exemplified in one embodiment by a monoclonal antibody designated DCGM4.

The mammalian protein defined, e.g., selectively recognized, by the antibody DCGM4 is designated Langerin. The natural Langerin protein mediates various physiological responses leading to biological or physiological responses in target cells. In particular, Langerhans DC cells are responsible for antigen presentation, e.g., presentation of haptens in hypersensitivity reactions. The DCGM4 antibody modulates various immunological responses which affect DC maturation and antigen presentation.

Langerin is a 40 kDa N-glycosylated protein. Immunoprecipitation with DCGM4 from DC extracts and, subsequent elution with SDS-PAGE sample buffer yielded a homogeneous band of 40–42 kDa molecular mass. If DTT was omitted all along the purification steps, the profile was not modified on the gel, suggesting that Langerin is present at the cell membrane as a single chain or as an homodimer with non-covalent association. Two dimensional analysis confirmed the molecular mass of the molecule and indicated a pI of 5.2–5.5. Finally, Langerin is a glycoprotein, and most of the carbohydrate constituents were removed by N-glycosylase treatment.

A gene encoding human langerin has now been cloned. The nucleotide sequence is showing in SEQ ID NO:1. The predicted amino acid sequence is shown in SEQ ID NO: 2. The predicted protein is a type II membrane lectin, with a calcium-dependent carbohydrate recognition domain. Amino acid homology with the Kupffer receptor of mouse, rat and chicken was found and provides support that langerin functions as a langerhans cell specific receptor for antigen capture. The carbohydrate recognition domain motif EPN supports that the sugar moieities are probably mannose and glucose.

Identifying characteristics that permit one of ordinary skill in the art to distinguish Langerin from other proteins are listed below.

binds with specificity to DCGM4 monoclonal antibody
 N-glycosylated form of protein ~40 kD, both reduced or non-reduced with a pI of 5.2–5.5 and lacking interchain disulfide bonds
 expressed on subset of DC cells
 normally expressed on the cell surface of Langerhans cells after binding with DCGM4, Langerin is transported within endocytic coated pits and participates in cytomembrane sandwiching; subsequently Langerin is associated with Birbeck granules.

Cells of the clonally derived hybridoma cell line designated DCGM4 from which mAb DCGM4 has been purified have been deposited with the American Type Culture Collection (ATCC), 10801 University Boulevard, Manassas Va., USA, on Sep. 22, 1998 under ATCC Accession Number No. HB-12576.

It is to be understood that this invention is not limited to the particular methods, compositions and antibodies described herein, as such methods, compositions and antibodies may, of course, vary. It is also to be understood that the terminology used herein is for the purpose of describing particular embodiments only, and is not intended to limit the scope of the present invention which is only limited by the appended claims.

II. Antibodies

Antibodies can be raised to the various mammalian, e.g., primate Langerin proteins and fragments thereof, both in naturally occurring native forms and in their recombinant forms, the difference being that antibodies to the active Langerin are more likely to recognize epitopes which are only present in the native conformations. Denatured antigen detection can also be useful in, e.g., Western analysis. Anti-idiotypic antibodies are also contemplated, which would be useful as agonists or antagonists of a natural Langerin protein or an antibody.

Antibodies, including binding fragments and single chain versions, against predetermined fragments or the whole of the protein (e.g., a protein having an amino acid sequence shown in SEQ ID NO: 2) can be raised by immunization of animals. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies, exemplified by the DCGM4, including antigen binding fragments, can have significant diagnostic or therapeutic value. They can be potent antagonists that bind to Langerin and inhibit binding partner interaction or inhibit the ability of the interaction to mediate a biological response. They also can be useful as non-neutralizing antibodies and can be coupled to toxins or radionuclides so that when the antibody binds to the antigen, a cell expressing it, e.g., on its surface, is killed. Further, this antibody can be conjugated to drugs or other therapeutic agents, either directly or indirectly by means of a linker, and may effect drug targeting.

The antibodies of this invention can also be useful in diagnostic applications. As capture or non-neutralizing antibodies, they might bind Langerin without inhibiting Langerin function on cells of the immune system, for example immature DC. As neutralizing antibodies, they can be useful in competitive binding assays. They will also be useful in detecting or quantifying Langerin protein or its binding partners. They may be used as reagents for Western blot analysis, or for immunoprecipitation or immunopurification of the Langerin protein. They will also be useful in evaluating cell populations to determine, e.g., the physiological state of an immune system.

Antigen fragments may be joined to other materials, particularly polypeptides, as fused or covalently joined polypeptides to be used as immunogens. The antigen may be purified as described below, including immunoaffinity methods using antibodies, e.g., DCGM4. An antigen and its fragments may be fused or covalently linked to a variety of carriers, such as keyhole limpet hemocyanin, bovine serum albumin, tetanus toxoid, etc. See, e.g., *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York, each of which are incorporated herein by reference, for descriptions of methods of preparing polyclonal antisera. A typical method involves hyperimmunization of an animal with the antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or, alternatively, selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; or made in transgenic mice, see Mendez, et al. (1997) *Nature Genetics* 15:146–156. These patents are incorporated herein by reference.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified Langerin protein will be released. Alternatively, the antibody may be used to quantitate and identify fractionated samples containing the antigen. Standard protein purification procedures, e.g., chromatography, will be used to enrich and purify Langerin protein with, e.g., ELISA assays, to identify fractions where Langerin separates.

Purified protein will be sequenced. The sequence will allow selection of oligonucleotide sequences useful as primers or probes. Alternatively, the sequence allows production of polypeptide segments for making additional antibodies. In addition, purified protein may be used for immunization, allowing production of polyclonal or monoclonal antibodies.

The antibodies may also be used to screen expression libraries for particular expression products. Usually the antibodies used in such a procedure will be labeled with a moiety allowing easy detection of presence of antigen by antibody binding. This will allow isolation of a cell which expresses a nucleic acid, e.g., a vector, encoding the antigen by, e.g., fluorescence activated cell sorting (FACS) analysis, and enrichment. Alternatively, an affinity method using antibodies of this invention can be used to immobilize and separate cells expressing the Langerin, e.g., encoded on a vector.

Antibodies raised against each Langerin protein will also be useful to raise anti-idiotypic antibodies. These will be useful in detecting or diagnosing various immunological conditions related to expression of the respective antigens.

III. Purified Langerin Protein

Human Langerin protein can be isolated from natural sources using standard biochemical purification techniques and/or by use of the antibody to determine the presence of the antigen in particular fractionation procedures. The purified proteins allow both sequence determination and preparation of peptides to generate further antibodies to recognize such segment. As used herein, Langerin shall encompass, when used in a protein context, a protein which, in a natural state, exhibits the properties listed above, or a significant fragment of such a protein. e.g., a protein having an amino acid sequence set forth in SEQ ID NO: 2 or a subsequence thereof. It also refers to a mammalian, e.g., primate, derived polypeptide which exhibits similar biological function or interacts with Langerin protein specific binding components. These binding components, e.g., antibodies, typically bind to a Langerin protein with high affinity, e.g., at least about 100 nM, usually better than about 30 nM, preferably better than about 10 nM, and more preferably at better than about 3 nM. One such preferred binding component is the antibody DCGM4.

The purified protein or peptide fragments are useful for generating antibodies by standard methods, as described below. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual Cold Spring Harbor Press.*

The term polypeptide, as used herein, includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Preferably, the fragment exhibits a biological property in common with the full length Langerin, e.g., immunological activity, including sharing of an epitope.

Substantially pure, in the polypeptide context, typically means that the protein is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. The analysis may be weight or molar percentages, evaluated, e.g., by gel staining, spectrophotometry, or terminus labeling.

A binding composition or agent refers to molecules that bind with specificity to Langerin protein, e.g., in a ligand-receptor type fashion, an antibody-antigen interaction, or compounds, e.g., proteins which specifically associate with Langerin protein, e.g., in a natural physiologically relevant protein—protein interaction, either covalent or non-covalent. The molecule may be a polymer, or chemical reagent. This implies both binding affinity and binding specificity or selectivity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman, et al. (eds. 1990) *Goodman & Gilman's: The Pharmacological Bases of Therapeutics* (8th ed.) Pergamon Press, Tarrytown, N.Y.

Soluble fragments of both the antibodies and Langerin antigens are provided by the invention. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

A Langerin protein that specifically binds to or that is specifically immunoreactive with an antibody generated against a defined immunogen, such as an immunogen consisting of the Langerin protein of the invention is typically determined in an immunoassay. The immunoassay typically uses a polyclonal antiserum which was raised, e.g., to a Langerin protein of the invention. This antiserum is selected to have low crossreactivity against other potential Langerin family members, e.g., allelic variants of Langerin proteins preferably from the same species, and any such crossreactivity is removed by immunoabsorption prior to use in the immunoassay.

To produce antisera for use in an immunoassay, the Langerin protein of the invention is isolated as described herein. For example, after determining the Langerin nucleic acid sequence using the methods described herein, a recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from a Langerin nucleic acid sequence can be conjugated to a carrier protein and subsequently used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other Langerin variants e.g., Langerin allelic variants, using a competitive binding immunoassay such as the one described in Harlow and Lane, supra, at pages 570–573. Preferably at least two Langerin variants are used in this determination. These Langerin family members can be produced as recombinant proteins and isolated using standard molecular biology and protein chemistry techniques as described herein.

Immunoassays in the competitive binding format can be used for the crossreactivity determinations. For example, the Langerin protein of the invention can be immobilized to a solid support. Proteins added to the assay compete with the binding of the antisera to the immobilized antigen. The ability of the above proteins to compete with the binding of the antisera to the immobilized protein is compared to a Langerin protein. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second Langerin protein to the immunogen protein (e.g., a Langerin allelic variant). To make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

It is understood that the Langerin protein of the invention is not only the protein characterized herein, but also to other Langerin proteins that are allelic, non-allelic, or species variants. It is also understood that the terms include non-natural mutations introduced by deliberate mutation using conventional recombinant technology such as single site mutation, or by excising short sections of DNA encoding the respective proteins, or by substituting new amino acids, or adding new amino acids to a Langerin sequence. Such minor alterations typically will substantially maintain the immunoidentity of the original molecule and/or its biological activity. Thus, these alterations include proteins that are specifically immunoreactive with a designated naturally occurring Langerin protein. The biological properties of altered proteins can be determined by expressing the protein in an appropriate cell line and measuring the appropriate effect, e.g., upon DC cells in vitro. Particular protein modifications considered minor include conservative substitution of amino acids with similar chemical properties. By aligning a protein optimally with the protein of the Langerins and by using conventional immunoassays as described herein to determine immunoidentity, one can determine the protein compositions of the invention.

IV. Physical Variants

This invention also encompasses proteins or peptides having substantial amino acid sequence homology with a natural mammalian Langerin protein or an antibody described above. The variants include species and allelic variants. A person having ordinary skill in the art will recognize that much of the following discussion of variants will apply to variants of both the Langerin antigen and the antibodies which recognize it.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the Langerin protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.; each of which is incorporated herein by reference.

An isolated DNA, isolated as described below, encoding a Langerin protein can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant Langerin protein derivatives include predetermined or site-specific mutations of the respective protein or its fragments. "Mutant Langerin protein" encompasses a polypeptide otherwise falling within the homology definition of the human Langerin protein as set forth above, but having an amino acid sequence which differs from that of Langerin protein as found in nature, whether by way of deletion, substitution, or insertion. In particular, "site specific mutant Langerin protein" generally includes proteins having significant homology with a natural protein with properties described herein, and/or sharing various biological activities, e.g., antigenic or immunogenic, with those sequences, and in preferred embodiments include, e.g., singly substituted natural forms of the proteins. Similar concepts apply to different Langerin proteins, particularly those found in various mammals, e.g., primates, including human. As stated before, it is emphasized that the descriptions are generally meant to encompass all mammalian Langerin proteins.

Although site specific mutation sites are predetermined, mutants need not be site specific. Langerin protein mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a Langerin polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of biologically relevant domains and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

V. Functional Variants

The blocking of physiological response mediated by Langerin proteins may result from the inhibition of binding of the antigen to its natural binding partner, e.g., through competitive inhibition. Thus, in vitro assays of the present invention will often use isolated protein, membranes from cells expressing a recombinant membrane associated Langerin protein, soluble fragments comprising binding segments, or fragments attached to solid phase substrates. These assays will also allow for the diagnostic determination of the effects of either binding segment mutations and modifications, or protein mutations and modifications, e.g., analogs. In particular, the Langerin is expressed on DC clones, but the antigen is lost after DC cell maturation.

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the Langerin protein and soluble fragments of the antigen which contain a high affinity binding site, can be used to inhibit antigen function in cells or tissues, e.g., cells or tissues experiencing abnormal or undesired physiology. "Derivatives" of the Langerin antigens, and of antibodies, include amino acid sequence mutants, glycosylation variants, and covalent or aggregate conjugates with other chemical moieties. Covalent derivatives can be prepared by linkage of functionalities to groups which are found in the Langerin amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the Langerin protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the Langerin proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of amino acids of the antigen, e.g., a binding segment, so that the presence or location of the fused antigen may be easily determined. See, e.g., Dull, et al. U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (Cur. ed.), Vols. 1–3, Cold Spring Harbor Laboratory, which are incorporated herein by reference. Techniques for synthesis of polypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; and Dawson, et al. (1994) *Science* 266:776–779; each of which is incorporated herein by reference.

This invention also contemplates the use of derivatives of the Langerin proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, a Langerin antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-Langerin protein antibodies or other binding partner. Langerin antigens can also be labeled with a detectable group, for example radioiodinated by the chloramine T procedure, covalently bound to rare earth chelates, or conjugated to another fluorescent moiety for use in diagnostic assays. Purification of Langerin protein may be effected by immobilized antibodies or binding partners.

A solubilized Langerin antigen or fragment of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, antigen binding fragments of natural antibodies are often equivalent to the antibodies themselves. Purified Langerin protein can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce further antibodies of the present invention, as described immediately below. For example, this invention contemplates antibodies raised against amino acid sequences from proteins having properties described in Table 1, or fragments of them. In particular, this invention contemplates antibodies having binding affinity to or being raised against specific fragments which are predicted to lie outside of the lipid bilayer, e.g., either extracellular or intracellular domain structures.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

Isolated genes will allow transformation of cells lacking expression of a corresponding Langerin protein, e.g., either species types or cells which lack corresponding antigens and should exhibit negative background biological activity. Expression of transformed genes will allow isolation of antigenically pure cell lines, with defined or single specie variants. This approach will allow for more sensitive detection and discrimination of the physiological effects of Langerin protein. Subcellular fragments, e.g., cytoplasts or membrane fragments, can also be isolated and used.

Dissection of the critical structural elements which effect the various physiological or differentiation functions provided by the proteins is possible using standard techniques of modern molecular biology, particularly in comparing members of a related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390; each of which is incorporated herein by reference.

In particular, functional domains or segments can be substituted between species variants or related proteins to determine what structural features are important in both binding partner affinity and specificity, as well as signal transduction. An array of different variants will be useful to screen for molecules exhibiting combined properties of interaction with different species variants of binding partners.

Antigen internalization may occur under certain circumstances, and interaction between intracellular components and "extracellular" segments of proteins involved in interactions may occur. The specific segments of interaction of Langerin with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of Langerin will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogs exhibiting agonist or antagonist properties on binding partners. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to antigen-binding partner interaction. Although the foregoing description has focused primarily upon the human Langerin protein, those of skill in the art will immediately recognize that the invention encompasses other closely related antigens, e.g., other primate species or allelic variants, as well as variants and other members of the family.

VI. Nucleic Acids

The properties of natural Langerin protein disclosed herein allow for purification of the protein. This provides means to isolate nucleic acids encoding such proteins, and determination of the sequence provides a handle to other members of the Langerin family. Such nucleotide sequences and related reagents are useful in constructing a DNA clone useful for expressing Langerin protein, or, e.g., isolating a homologous gene from another natural source, including other members of the family. Typically, the sequences will be useful in isolating other genes, e.g., allelic variants or alternatively spliced isoforms, from human.

For example, a specific binding composition such as DCGM4 could be used for screening of an expression library made from a cell line which expresses a Langerin protein. The screening can be standard staining of surface expressed protein, or by panning. Screening of intracellular expression can also be performed by various staining or immunofluorescence procedures. The binding compositions could be used to affinity purify or sort out cells expressing the Langerin protein.

This invention contemplates use of isolated DNA or fragments to encode a biologically active Langerin protein or Langerin polypeptide. A nucleotide sequence encoding human langerin is shown in SEQ ID NO: 1. In addition, this invention covers isolated or recombinant DNA which encodes a biologically active Langerin protein or Langerin polypeptide and which is capable of hybridizing under appropriate conditions with the DNA sequences. Said biologically active Langerin protein or Langerin polypeptide can be a full length antigen, or fragment thereof. Further, this invention covers the use of isolated or recombinant DNA, or fragments thereof, which encode proteins which are homologous to a Langerin protein or which were isolated using cDNA encoding a Langerin protein as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term "isolated" nucleic acid embraces a nucleic acid sequence which has been removed from its naturally occurring environment, and it also includes recombinant or cloned DNA isolates and chemically synthesized analogs or analogs biologically synthesized by heterologous systems. A substantially pure molecule includes isolated forms of the molecule. Alternatively, a purified species may be separated from host components from a recombinant expression system.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, synthetic oligonucleotides are used to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant polypeptide, e.g., a fusion polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A DNA which codes for a Langerin protein will be particularly useful to identify genes, mRNA, and cDNA species which code for related or homologous proteins, as well as DNAs which code for homologous proteins. There should be homologues in other mammals, e.g., primates. Various Langerin proteins should be homologous and are encompassed herein. However, even proteins that have a more distant evolutionary relationship to the antigen can readily be isolated under appropriate conditions using these sequences if they are sufficiently homologous. Primate Langerin proteins are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (ed. 1987) *Teratocarcinomas and Embryonic Stem Cells: A Practical Approach* IRL Press, Oxford; Rosenberg (1992) *J. Clinical Oncology* 10:180–199; and Cournoyer and Caskey (1993) *Ann. Rev. Immunol.* 11:297–329; each of which is incorporated herein by reference.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence as described. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370; Walker (ed. 1988) *New Nucleic Acid Techniques* Humana Press, Clifton, N.J.; Ross (ed. 1998) *Nucleic Acid Hybridization*; Wiley, New York; or see, e.g., recent hybridization protocols on the Internet in "A Selection of Molecular Biology Protocols—A list of sites with protocols," by Griffin (1996) *Analytical Biochemistry* 239:120–122.

VII. Making Langerin Protein; Mimetics

Langerin may be isolated from natural sources using standard methods of protein biochemistry. The DCGM4 antibody may be used to track the purification process, or in various immunoaffinity methods. Isolated protein may be used as starting material for derivatization or modification. The protein may be used in native or denatured forms.

DNA which encodes the Langerin protein or fragments thereof can be obtained by chemical synthesis, screening cDNA libraries, or by screening genomic libraries prepared from a wide variety of cell lines or tissue samples. In particular, the DCGM4 antibody may be used to expression clone the nucleic acid encoding the protein antigen.

This DNA can be expressed in a wide variety of host cells for the synthesis of a full-length protein or fragments which can in turn, for example, be used to generate polyclonal or monoclonal antibodies; for binding studies; for construction and precision of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier, buffer, and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a Langerin protein, or a fragment thereof, preferably encoding a biologically active polypeptide. The sequence set forth in SEQ ID NO: 1 may advantageously be used to prepare Langerin protein. The DNA can be under the control of a viral promoter and can encode a selection marker. This invention further contemplates use of such expression vectors which are capable of expressing eukaryotic cDNA coding for a Langerin protein. in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of a Langerin gene or its fragments into the host DNA by recombination, or to integrate a promoter which controls expression of an endogenous gene e.g., see WO 96/29411 (incorporated herein by reference including all figures and drawings) describing such technology.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N. Y.; and Rodriquez, et al. (eds. 1988) *Vectors: A Survey of Molecular Cloning Vectors and Their Uses*, Buttersworth, Boston, Mass.; which are incorporated herein by reference.

Transformed cells include cells, preferably mammalian, that have been transformed or transfected with vectors containing a Langerin nucleic acid sequence, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide, a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the Langerin proteins or its fragments include, but are not limited to, such vectors as those containing the lac promoter (pUC-series); trp promoter (pBR322-trp);

Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236, which is incorporated herein by reference.

Lower eukaryotes, e.g., yeasts and Dictyostelium, may be transformed with vectors encoding Langerin proteins. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active Langerin protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMClneo Poly-A, see Thomas, et al. (1987) *Cell* 51:503–512; and a baculovirus vector such as pAC 373 or pAC 610.

It will often be desired to express a Langerin protein polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the Langerin protein gene may be co-transformed with one or more genes encoding mammalian or other glycosylating enzymes. Using this approach, certain mammalian glycosylation patterns will be achievable or approximated in prokaryote or other cells.

The Langerin protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. BioPhys. Acta* 988:427–454; Tse, et al. (1985) *Science* 230:1003–1008; and Brunner, et al. (1991) *J. Cell Biol.* 114:1275–1283.

Fragments or derivatives of Langerin can be prepared by conventional processes for synthesizing peptides. Solid phase and solution phase syntheses are both applicable to the foregoing processes. These include processes such as are described in Bodanszky (1993) *Principles of Peptide Synthesis*; Springer-Verlag; Bodanszky (1994) *The Practice of Peptide Synthesis*; Springer-Verlag; Jones (1992) *Amino Acid and Peptide Synthesis*; Oxford University Press; Atherton and Sheppard (1989) *Solid Phase Peptide Synthesis: A Practical Approach*; IRL Press New York; Stewart and Young (1984) *Solid Phase Peptide Synthesis*, Pierce Chemical Co., Rockford, Ill.; and chemical ligation, e.g., Dawson, et al. (1994) *Science* 266:776–779, a method of linking long synthetic peptides by a peptide bond; each of which is incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The Langerin protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156, which is incorporated herein by reference.

The prepared protein and fragments thereof can be isolated and purified from the reaction mixture by means of peptide separation, for example, by extraction, precipitation, electrophoresis and various forms of chromatography, and the like. The Langerin of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing Langerin protein as a result of DNA techniques, see below.

VIII. Utility

The present invention provides reagents which will find use in diagnostic applications as described elsewhere herein, e.g., in the general description for physiological or developmental abnormalities, or below in the description of kits. The antigen will be useful in both diagnostic methods, for isolating various cell types, e.g., Langerhans cells, or for forensic methods to determine various species sources of biological samples.

This invention provides reagents with significant therapeutic value. Langerin (naturally occurring or recombinant), fragments thereof, muteins, and antibodies, along with compounds identified as having binding affinity to Langerin or antibodies, find use in the treatment of conditions exhibiting abnormal expression of Langerin of its ligands or binding agents. Such abnormality will typically be manifested by immunological disorders. Additionally, this invention provides therapeutic value in various diseases or disorders associated with abnormal expression or abnormal triggering of response to the ligand or binding agent. The Langerin ligands or binding agents are suspected to be involved in maturational development of DC. Langerin may also be used as a receptor to target antigen to dendritic cells to elicit therapeutically relevant immune responses.

Recombinant Langerins, muteins, agonist or antagonist antibodies thereto, or antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates the use of antibodies or binding fragments thereof which are not complement binding.

Using Langerin or fragments thereof to screen for binding partner or for compounds having binding affinity to Langerin antigen can be performed including the isolation of associated compounds. Subsequent biological assays can then be utilized to determine if a putative ligand or binding agent can provide competitive binding, which can block intrinsic stimulating activity. Langerin fragments can be used as a blocker or antagonist in that it blocks the activity of ligand or binding agent. This invention further contemplates the therapeutic use of antibodies to Langerins as antagonists. This approach will be particularly useful with other Langerin protein species variants and other members of the family.

The quantities of reagents necessary for effective therapy will depend upon many different factors, including means of administration, target site, reagent physiological life, pharmacological life, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. The actual dosage of reagent, formulation or composition that modulates an immunological disorder depends on many factors, including the size and health of an organism, however, one of ordinary skill in the art can use teachings describing methods and techniques for determining clinical dosages. See, e.g., Spilker (1984) *Guide to Clinical Studies and Developing Protocols*, Raven Press Books, Ltd., New York, esp. pp. 7–13, 54–60; Spilker (1991) *Guide to Clinical Trials*, Raven Press, Ltd., New York, esp. pp. 93–101; Craig and Stitzel (eds. 1986) *Modern Pharmacology*, 2d ed., Little, Brown and Co., Boston, esp. pp. 127–33; Speight (ed. 1987) *Avery's Drug Treatment: Principles and Practice of Clinical Pharmacology and Therapeutics*, 3d ed., Williams and Wilkins, Baltimore, esp. pp. 50–56; Tallarida, et al. (1988) *Principles of General Pharmacology*, Springer-Verlag, New York, esp. pp. 18–20; Gilman, et al. (eds.) *Goodman and Gilman's: The Pharmacological Bases of Therapeutics*, latest ed., Pergamon Press; *Remington's Pharmaceutical Sciences*, latest ed., Mack Publishing Co., Easton, Pa.; and Rich, et al. (1998) *Clinical Immunology: Principles and Practice Vols. I & II*, Mosby, St. Louis, Mo., each of which is hereby incorporated herein by reference in its entirety including all drawings and figures. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Because of the likely high affinity binding, or turnover numbers, between a putative ligand or binding agent and its binding partner, low dosages of these reagents would be initially expected to be effective. Thus, dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

Other abnormal developmental conditions are known in the cell types shown to possess Langerin antigen, e.g., DC cells and epithelial cells of the tonsil. See Brew (ed.) *The Merck Manual of Diagnosis and Therapy* Merck & Co., Rahway, N.J.; and Thorn, et al. *Harrison's Principles of Internal Medicine* McGraw-Hill, N.Y. These problems may be susceptible to prevention or treatment using compositions provided herein.

Langerins, fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by methods well known in the art of pharmacy. See, e.g., Gilman, et al. (eds. 1990) *Goodman and Gilman's: The Pharmacological Bases of Therapeutics,* 8th Ed., Pergamon Press; and *Remington's Pharmaceutical Sciences,* current ed., Mack Publishing Co., Easton, Pa.; Avis, et al. (eds. 1993) *Pharmaceutical Dosage Forms: Parenteral Medications* Dekker, N Y; Lieberman, et al. (eds. 1990) *Pharmaceutical Dosage Forms: Tablets* Dekker, N Y; and Lieberman, et al. (eds. 1990) *Pharmaceutical Dosage Forms: Disperse Systems* Dekker, N Y. The therapy of this invention may be combined with or used in association with other therapeutic agents.

Both the naturally occurring and the recombinant forms of the Langerin specific antibodies and the Langerin proteins of this invention are particularly useful in kits and assay methods which are capable of screening compounds for binding activity. Several methods of automating assays have been developed in recent years so as to permit screening of tens of thousands of compounds in a short period. See, e.g., Fodor, et al. (1991) *Science* 251:767–773, which is incorporated herein by reference and which describes means for testing of binding affinity by a plurality of defined polymers synthesized on a solid substrate. The development of suitable assays can be greatly facilitated by the availability of large amounts of purified, soluble Langerin protein as provided by this invention.

This invention is particularly useful for screening compounds by using recombinant antigen in any of a variety of drug screening techniques. The advantages of using a recombinant protein in screening for specific ligands or binding agents include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood, et al. *Immunology* Benjamin/Cummings; Paul (ed. 1996) *Fundamental Immunology* 3d ed, Raven Press, NY; and *Methods in Enzymology* Academic Press. This will also be useful in screening for a ligand which binds a Langerin, e.g., from an interacting cell.

One method of drug screening utilizes eukaryotic or prokaryotic host cells which are stably transformed with recombinant DNA molecules expressing the Langerin antigens. Cells may be isolated which express an antigen in isolation from other functionally equivalent antigens. Such cells, either in viable or fixed form, can be used for standard protein—protein binding assays. See also, Parce, et al. (1989) *Science* 246:243–247; and Owicki, et al. (1990) *Proc. Nat'l Acad. Sci. USA* 87:4007–4011; which are incorporated herein by reference and describe sensitive methods to detect cellular responses. Competitive assays are particularly useful, where the cells (source of Langerin protein) are contacted and incubated with a labeled binding partner or antibody having known binding affinity to the ligand, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Numerous techniques can be used to separate bound from free antigen to assess the degree of binding. This separation step could typically involve a procedure such as adhesion to filters followed by washing, adhesion to plastic followed by washing, or centrifugation of the cell membranes. Viable cells could also be used to screen for the effects of drugs on Langerin protein mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as a source of Langerin protein. These cells are stably transformed with DNA vectors directing the expression of a membrane associated Langerin protein, e.g., an engineered membrane bound form. Essentially, the membranes would be prepared from the cells and used in a receptor/ligand type binding assay such as the competitive assay set forth above.

Still another approach is to use solubilized, unpurified or solubilized, purified Langerin protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to Langerin and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified Langerin binding composition, and washed. The next step involves detecting bound binding composition.

Rational drug design may also be based upon structural studies of the molecular shapes of the Langerin protein and other effectors or analogs. Effectors may be other proteins which mediate other functions in response to antigen binding, or other proteins which normally interact with the antigen, e.g., Langerin ligand. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

Purified Langerin protein can be coated directly onto plates for use in the aforementioned drug screening techniques. However, non-neutralizing antibodies to these ligands can be used as capture antibodies to immobilize the respective ligand on the solid phase.

IX. Kits and Quantitation/Detection

Both naturally occurring and recombinant forms of the Langerin molecule of the invention are particularly useful in kits and assay methods. For example, these methods would also be applied to screening for binding activity, e.g., ligands or binding agents for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767–773, which is incorporated herein by reference. The latter describes means for testing binding by an agent by a plurality of defined polymers synthesized on a solid substrate. The development of suitable assays to screen for a ligand or binding agent or agonist/antagonist homologous proteins can be greatly facilitated by the availability of large amounts of purified, soluble Langerin in an active state such as is provided by this invention.

Purified Langerin can be coated directly onto plates for use in the aforementioned ligand or binding agent screening techniques. However, non-neutralizing antibodies to these proteins can be used as capture antibodies to immobilize the respective Langerin protein on the solid phase, useful, e.g., in diagnostic uses.

This invention also contemplates use of Langerin, fragments thereof, peptides, and their fusion products in a variety of diagnostic kits and methods for detecting the presence of the Langerin protein or its ligand or binding agent. Alternatively, or additionally, antibodies against the Langerin molecules may be incorporated into the kits and methods. Typically the kit will have a compartment containing either a Langerin protein, fragment, peptide or gene segment or a reagent which recognizes one or the other of these. Typically, recognition reagents, in the case of a protein or fragment thereof, would be a receptor or antibody, or in the case of a gene segment, would usually be a hybridization probe.

A preferred kit for determining the concentration of Langerin in a sample would typically comprise a labeled compound, e.g., ligand, binding agent, or antibody, having known binding affinity for Langerin, a source of Langerin (naturally occurring or recombinant) as a positive control, and a means for separating the bound from free labeled compound, for example a solid phase for immobilizing the Langerin in the test sample. Compartments containing reagents, and instructions, will normally be provided.

This invention also contemplates use of Langerin proteins, fragments thereof, peptides, their fusion products, and binding compositions in a variety of diagnostic kits and methods for detecting the presence of a binding composition. Typically the kit will have a compartment containing either a defined Langerin peptide or gene segment or a reagent which recognizes one or the other, e.g., antigen fragments or antibodies. See, e.g., Chen (ed.)(1987) *Immunoassay: A Practical Guide* Academic Press, Orlando, Fla.; Price and Newman (eds.)(1991) *Principles and Practice of Immunoassay* Stockton Press, New York; and Ngo (ed.) (1988) *Nonisotopic Immunoassay* Plenum Press, NY.

A kit for determining the binding affinity of a test compound to a Langerin protein would typically comprise a test compound; a labeled compound, for example an antibody having known binding affinity for the antigen; a source of Langerin protein (naturally occurring or recombinant); and a means for separating bound from free labeled compound, such as a solid phase for immobilizing the antigen. Once compounds are screened, those having suitable binding affinity to the antigen can be evaluated in suitable biological assays, as are well known in the art, to determine whether they exhibit similar biological activities to the natural antigen. The availability of recombinant Langerin protein polypeptides also provide well defined standards for calibrating such assays.

One method for determining the concentration of Langerin protein in a sample would typically comprise the steps of: (1) preparing membranes from a sample comprised of a membrane bound Langerin protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the Langerin protein or fragments are useful in diagnostic applications to detect the presence of elevated levels of Langerin protein and/or its fragments. Such diagnostic assays can employ lysates, live cells, fixed cells, immunofluorescence, cell cultures, tissue samples, body fluids, and further can involve the detection of antigens related to the protein in serum, or the like. Diagnostic assays may be homogeneous (without a separation step between free reagent and protein—protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a Langerin protein or to a particular fragment thereof. Similar assays have also been extensively discussed in the literature. See, e.g., Harlow and Lane (1988) *Antibodies: A Laboratory Manual*, CSH, and Coligan (ed. 1991) and periodic supplements, *Current Protocols In Immunology* Greene/Wiley, New York.

Anti-idiotypic antibodies may have similar use to diagnose presence of antibodies against a Langerin protein, as such may be diagnostic of various abnormal states. For example, overproduction of Langerin protein may result in production of various immunological reactions which may be diagnostic of abnormal physiological states associated with Langerhans cells (e.g., atopic dermatitis, eosinophilic granuloma, histiocytosis, systemic sclerosis and Langerhans cell granulomatosis). Also, see, e.g., Rich, et al. (1998) *Clinical Immunology: Principles and Practice Vols. I & II*, Mosby, St. Louis, Mo.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled Langerin protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In these assays, the antigen, test compound, Langerin protein, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free antigen, or alternatively the bound from the free test compound. The Langerin protein can be immobilized on various matrices followed by washing. Suitable matrices include plastic such as an ELISA plate, filters, and beads. Methods of immobilizing the Langerin protein to a matrix include, without limitation, direct adhesion to plastic, use of a capture antibody, chemical coupling, and biotin-avidin. The last step in this approach involves the precipitation of protein—protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678, each of which is incorporated herein by reference.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a Langerin protein. These sequences can be used as probes for detecting levels of antigen message in samples from patients suspected of having an abnormal condition, e.g., an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like.

Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

X. Isolating Langerin Specific Binding Partners

The description of the Langerin protein herein provides means to identify Langerin ligands or binding agents, as described above. Such a ligand or binding agent should bind specifically, e.g., selectively, to the Langerin or fragment thereof with reasonably high affinity. Typical ligand or binding agent binding constants will be at least about 30 mM, e.g., generally at least about 3 mM, more generally at least about 300 $\mu$M, typically at least about 30 $\mu$M, 3 $\mu$M, 300 nM, 30 nM, etc. Various constructs are made available which allow either labeling of Langerin to detect its ligand or binding agent. For example, directly labeling Langerin, fusing onto it markers for secondary labeling, e.g., FLAG or other epitope tags, etc., will allow detection of a binding agent or ligand. This can be histological, as an affinity method for biochemical purification, or labeling or selection in an expression cloning approach. A two-hybrid selection system may also be applied making appropriate constructs with the available Langerin sequences. See, e.g., Fields and Song (1989) *Nature* 340:245–246.

The Langerin protein should interact with a ligand based, e.g., upon its similarity in structure and function to other cell markers exhibiting developmental and cell type specificity of expression. Methods to isolate a ligand are made available by the ability to make purified Langerin for screening programs. Soluble or other constructs using the Langerin sequences provided herein will allow for screening or isolation of Langerin specific ligands.

Generally, descriptions of Langerins will be analogously applicable to individual specific embodiments directed to Langerin and/or Langerin reagents and compositions.

Without further elaboration, it is believed that a person of ordinary skill in the art can, using the preceding description, utilize the present invention to its fullest extent. The following examples are put forth solely for the purpose of illustration as to make and use the present invention, and are not intended, nor should they be construed, to limit the scope of what the inventors regard as their invention. Unless indicated otherwise below, parts are parts by weight, molecular weight is weight average molecular weight, temperature is in degrees Centigrade, and pressure is at or near atmospheric.

EXAMPLES

General Methods Some of the standard methods are described or referenced, e.g., in Maniatis, et al. (1982) *Molecular Cloning, A Laboratory Manual* Cold Spring Harbor Laboratory, Cold Spring Harbor Press; Sambrook, et al. (1989) *Molecular Cloning: A Laboratory Manual* (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology* Greene/Wiley, New York; Innis, et al. (eds. 1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1995 and supplements) *Current Protocols in Protein Science* John Wiley and Sons, New York, N.Y.; Matsudaira (ed. 1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.: which are incorporated herein by reference.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Example 1

Dendritic Cell Clones

Collection and Purification of Cord Blood CD34+ HPC

Umbilical cord blood samples were obtained according to standard institutional guidelines for human samples. Cells bearing CD34 antigen were isolated from mononuclear fractions by positive selection with Minimacs separation columns (Miltenyi Biotec, Bergish Gladbach, Germany), using an anti-CD34 mAb (Immu-133.3, Immunotech, Marseille, France) and goat anti-mouse IgG-coated microbeads (Miltenyi Biotec). In all experiments, isolated cells were 80–99% CD34+ as judged by staining with an anti-CD34 mAb.

Hematopoietic Factors

Recombinant human (rh) GM-CSF (specific activity: $2 \times 10^6$ U/mg; Schering-Plough Research Institute, Kenilworth, N.J.) was used at 100 ng/ml (200 U/ml); rhTNF-α (specific activity: $2 \times 10^7$ U/mg; Genzyme, Boston, Mass.) was used at 2.5 ng/ml (50 U/ml); rhSCF (specific activity: $4 \times 10^5$ U/mg; R&D, Abington, UK) was used at 25 ng/ml; rhIL-4 (specific activity: $10^7$ U/mg; Schering-Plough Research Institute) was used at 5 ng/ml; and rhTGF-β1 (R&D) was used at 1 ng/ml.

Dendritic Cell Generation from CD34+HPC

Cultures of CD34+ HPC were established as described in Caux, et al. (1992) *Nature* 392:258–261, in the presence of GM-CSF, SCF, and TNF-α, in endotoxin-free medium consisting of RPMI 1640 (Gibco BRL, Gaithersburg, Md.) supplemented with 10% heat-inactivated fetal bovine serum (FBS; Flow Laboratories, Irvine, UK), 10 mM Hepes, 2 mM L-glutamine, $5 \times 10^{-5}$ M 2-mercaptoethanol and gentamicin (80 μg/ml) (referred to as complete medium).

CD34+ cells were seeded in 25 to 75 cm² culture flasks (Corning, N.Y.; NY) at $2 \times 10^4$ cells/ml. Optimal conditions were maintained by splitting cultures at day 4 with medium containing fresh GM-CSF and TNF-a. In some experiments, TNF-α was replaced at day 7 by TGF-β. In other experiments, DC were activated at day 9 or day 12 with murine Ltk⁻ fibroblastic L cells stably transfected with the human CD40 ligand (L) gene (cell line established by Dr. C. van Kooten (van Kooten, et al. (1994) Eur J Immunol 24:787–92). Briefly, $10^5$ irradiated CD40L L cells (7,500 rads) were seeded together with 5 $10^5$ CD34-derived DC in presence of GM-CSF.

Isolation of Epidermal Cells

Epidermal cell suspensions were obtained from normal skin of patients undergoing reconstructive plastic surgery of the breast. Skin was split-cut with a keratome set and the dermo-epidermal slices treated for 18 h at 4° C. with 0.05% trypsin (Sigma) in Hank's balanced salt solution without $Ca^{2+}$ and $Mg^{2+}$ (Seromed, Biochrom KG, Berlin, FRG). The epidermis was detached from the dermis with fine forceps. Epidermal sheet cell suspensions were obtained by subsequent tissue dislocation and filtration through sterile gaze. Enrichment of Langerhans cells was obtained by density gradient centrifugation on Lymphoprep (Nycomed Pharma, Oslo, Norway).

Example 2

Antibodies and Flow Cytometry

For single cell staining, cells were labeled using the following mAbs: anti-E-cadherin (SHE 79.7; Takara, Shiga, Japan), anti-MHC class II (HLA-DR) (Becton Dickinson), and anti-Lag, all revealed by FITC-conjugated goat anti-mouse immunoglobulin (Dako, Glostrup, Denmark) For double staining, cells were labeled with mAb DCGM4 revealed by phycoerythrin(PE)-conjugated goat anti-mouse immunoglobulin (Dako), and after saturation in 5% mouse serum, with FITC-conjugated anti-CD1a (Ortho, Raritan, N.J.). Negative controls were performed with unrelated murine mAbs. Fluorescence was determined with a FACS-CAN flow-cytometer (Becton Dickinson). For intracytoplasmic phenotyping, cells were stained in PBS, 0.3% Saponin (Sigma) and 5% BSA, using the same procedure.

Example 3

Biochemistry

Proteins were extracted from CD34-derived DC supplemented with TGF-β by addition, to a frozen pellet of 100 μl/10⁷ cells, of 50 mM Tris-HCL pH 8 buffer with 150 mM NaCl, 5 mM EDTA, 1% Triton X100 and protease inhibitor (complete Mini, Boeringer Mannheim). After 1 h at 4° C., samples were centrifuged to remove cellular debris. Supernatants were then incubated 1 h at 4° C. with DCGM4 covalently linked to Dynabeads M-450 Sheep anti-mouse magnetic beads (Dynal, Oslo, Norway). Beads were washed with extraction buffer by using a Dynal magnetic particle-concentrator and boiled in the presence of 50 μl SDS-PAGE sample buffer or resuspended in 100 μl of 0.5 M Glycine, 0.15 M NaCl pH 2.3 for 4 minutes. Then, supernatant was neutralized with 3.5 μl of saturated Tris solution. SDS-PAGE analysis was performed with a PhastSystem in a 10–15% gradient gel (Pharmacia Biotech), and gels were stained with Coomassie R250. 2-D analysis was performed on a Multiphor II flat bed system with Immobiline DryStrip pH 3–10 and Excelgel SDS 8–18% for the second dimension (Pharmacia Biotech), and gels were silver stained. Dialyzed samples of proteins eluted from IgG linked to Dynabeads were digested with N-glycosidase F (Boehringer-Mannheim) at 37° C. overnight. Five microliters of original samples or 10 microliters of digested samples were deposited on nitrocellulose, and treated with DIG glycan detection kit (Boehringer-Mannheim).

Example 4

Purification of Langerin

DCGM4 expressing cells are used for large scale protein extraction. The protein is gently solubilized, and the resulting Langerin is purified using standard methods of protein purification. Chromatographic methods are used, and immunoaffinity techniques can be applied. The Langerin protein is followed by SDS PAGE and/or immunoassays. Diagnostic methods are used to ensure that the protein is substantially pure.

Purified protein is used for protein microsequencing. See, e.g., Matsudaira (ed. 1993) *A Practical Guide to Protein and Peptide Purification for Microsequencing*, Academic Press, San Diego, Calif. Sequence data is used to search sequence databases, e.g., GENBANK, to find natural genes encoding the Langerin.

Alternatively, the sequence data is useful for isolating a nucleic acid encoding Langerin using, e.g., degenerate PCR primers, etc.

Protein will also be used to raise additional antibodies. Such antibodies may be polyclonal or monoclonal. The protein can be used to assay and determine titers and affinity. Standard methods of immunization are available, as described above.

Example 5

Internalization Assay

CD34-derived DC supplemented with TGF-β were generated as detailed above and internalization was performed as described (Cella, et al. (1997) *J. Exp. Med.* 185:1743–51). One aliquot of cells was fixed with RPMI, 0.1% glutaraldehyde for 5 min. at room temperature and another aliquot was used without fixation. Both samples were stained with mAb DCGM4 or mAb DCGM1 for 40 min. on ice, and incubated with biotin-labeled F(ab')$_2$ goat anti-mouse IgG (Jackson ImmunoResearch Laboratories, PA) for 1 h on ice. Cells were then placed in a 37° C. water-bath for various time periods, cooled on ice and stained with PE-conjugated streptavidin (Becton Dickinson). After washing, cells were analyzed by FACS. The measure of internalization is given by the percentage decrease of cell-surface median fluorescence intensity (MFI) as compared to control samples kept at 4° C. The percentage decrease of MFI observed in fixed cells was taken as measure of the off-rate of the antibody at 37° C. Linear regression analysis of the plots of $\log_{10}$ (percentage of median fluorescence) vs. time was performed and rates of ingestion (k) and half-life ($t_{1/2}$) of membrane-bound complexes were calculated from the slope (m) of the resulting straight line using the relationships k(%/min)=−2, 303 m×100, and $t_{1/2}$ (min)=log2/m (Leslie,EJI 1980). In this mAb DCGM1 which recognizes the macrophage mannose receptor was generated by Applicant, and used as positive control for receptor-mediated endocytosis.

Example 6

Generation and Characterization of DCGM4 Monoclonal Antibodies

BALB/c mice (Iffa Credo, Les Oncins, France) were immunized with three intraperitoneal injections of CD34-derived DC ($10^6$ cells) with Freund's adjuvant (Sigma Chemical Co., St. Louis, Mo.). Three days after the final injection, splenocytes were fused with the murine myeloma cell line SP2, using polyethylene glycol-1000 (Sigma). Hybrid cells were placed in 96-well Falcon tissue culture plates (Falcon, Lincoln Park, N.J.) and fed with DMEM F12 (Life Technologies, Gaithersburg, Md.) supplemented with streptomycin (100 μg/ml), penicillin (100 U/ml), glutamine (2 mM), 10% horse serum (Life Technologies), 1% culture medium additive (CRTS, Lyon, France), $10^{-5}$ M azaserine (Sigma), and $5\times10^{-5}$ M hypoxanthine. Supernatants were screened for reactivity with CD34-derived DC and three unrelated cell types, namely peripheral blood polynuclear cells, T lymphocytes activated with PHA, and the myeloid cell line KG1 (ATCC; Rockville, Md.). Selected hybridomas were cloned by limiting dilution and ascites were produced in BALB/c mice. MAb DCGM4 was purified by anion-exchange chromatography on DEAE A50 (Pharmacia Biotech, Uppsala, Sweden) and coupled with fluorescein and biotin using standard procedures. Ig isotype was determined by ELISA using a mouse hybridoma subtyping kit (Boehringer-Mannheim, Mannheim, Germany).

Example 7

Immunohistology

Microscope slides of acetone-fixed cryocut tissue sections or cell cytospin preparations were incubated with mAbs for 60 min., and subsequently with biotinylated sheep anti-mouse Ig (The Binding Site, Birmingham, UK) for 30 min. Following incubation with streptavidin coupled to alkaline phosphatase (Biosource, CA, USA) for 30 min., enzyme activity was developed using Fast Red substrate (Dako). Double staining, with mouse IgG1 antibody DCGM4 and IgG2b anti-CD1a (Immunotech) were revealed by sheep anti-mouse IgG1 (The Binding Site) followed by mouse anti-alkaline phosphatase-alkaline phosphatase complexes (Dako) (APAAP technique), and biotinylated sheep anti-mouse IgG2b (The Binding Site) followed by ExtrAvidin-peroxydase (Sigma). The binding of goat anti-sIgD-biotin and DCGM4-biotin (for double staining with Lag) were directly revealed by ExtrAvidin-peroxidase. Alkaline phosphatase activity and peroxidase activity were respectively demonstrated using Fast Blue substrate (Sigma) and 3-amino-ethylcarbazole (Sigma).

Example 8

Electron Microscopy

Langerhans cell-enriched epidermal cell suspensions were incubated with control mouse IgG1 (Sigma), anti-CD1a (DMC1 mAb; REF), or DCGM4 for 1 h at 4° C. After washing, cells were incubated with a goat anti-mouse IgG conjugated with colloidal gold particles of 5 nM (GAM-nM) (Amersham, address, France) for 30 min. at 4° C. Cells were either fixed immediately for 18 hours with 2% glutaraldehyde in cacodylate buffer, followed by washing for at least 24 h in cacodylate buffer with sucrose, or warmed up to 37° C. or room temperature before fixation. Samples were post-fixed for 1 hour with 1% osmium in cacodylate buffer with sucrose, dehydrated, and embedded in Epoxy resin. Ultrathin sections were post-stained with uranyl acetate and lead citrate, and examined on a JEOL 1200 EX electron microscope (CMEABG, Université de Lyon, Lyon, France). A quantitative evaluation of cell-surface antigen density was performed according to Lafferty, et al. (1981) *J. Histochem Cytochem* 29:49–56. The number of gold granules bound along the cell membrane was counted and total circumference of the cell was measured on micrographs with a minimop morphometric analyzer (Zeiss). Results were expressed as number of gold granules per 100 μm of cell membrane. For each group of cells, counts were obtained from at least 20–30 cell sections. Mean and standard deviation were subsequently determined.

Example 9

Confocal Microscopy

Intracellular immunofluorescence staining was performed as previously described by Winzler, et al. (1997) *J. Exp. Med.* 185:317–28. Cells on polylysine coated coverslips and fixed for 15 min. with 4% paraformaldehyde, were washed in 10 mM glycine, then permeabilized with 0.5% saponin, 0.2% BSA for 30 min. Coverslips were incubated for 30 min. at room temperature with anti-LAMP-1 (Pharmingen, San Diego, Calif.), anti-HLA-DR (Becton Dickinson) or anti-Lag (Kashishara, et al. *J Invest Dermatol* 87:602–607) at a final concentration of 5 μg/ml in permeabilization medium. After three washes, cells were incubated for 30 min. with secondary labeled antibody (donkey anti-mouse coupled to Texas-red (Vector Laboratories, Burlingame, Calif.), washed, and incubated with mouse preimmune serum for 30 min., washed again, post-fixed with 2% paraformaldehyde, and finally incubated for 30 min. with mAb DCGM4 coupled to fluorescein (FITC). After washing, coverslips were mounted onto glass slides with fluoromount (Southern Biotechnology Associates Inc., Birmingham, Ala.). Confocal microscopy was performed using Confocal Laser Scanning Microscope TCS 4D (Leica Lasertechnik GmbH, Heidelberg, Germany) interfaced with an argon/krypton ion laser and with fluorescence filters and detectors allowing to simultaneously record FITC and Texas-red markers Rovere, et al. (1998) *Proc. Nat. Acad. Sci. USA* 95:1067–1072.

Example 10

Selection of Monoclonal Antibody DCGM4 Reactive Against Langerin

Supernatants from 854 hybridomas were screened for reactivity on DC obtained from CD34$^+$ HPC cultured 12 days in GM-CSF and TNF-α. In parallel, the supernatants were assayed for reactivity on three unrelated cell types, namely peripheral blood polynuclear cells, T lymphocytes activated with PHA and the myeloid cell line KG1. Supernatant from one hybridoma, designated DCGM4 was found to react only with a minor subset of DC and not with the other cell types of the differential screening.

The hybridoma was cloned by limiting dilution. The antibody was produced in ascites and subsequently purified using DEAE chromatography. MAb DCGM4 was found to be of IgG1/K isotype as determined by ELISA. As the observed reactivity restricted to a DC subset appeared of particular interest, mAb DCGM4 was selected for further studies. Finally, early experiments indicating that LC stained positive, we termed Langerin the antigen recognized by mAb DCGM4.

Example 11

Langerin is Selectively Expressed on Langerhans-Type Immature Dendritic Cells

CD34$^+$ HPC cultured with a combination of GM-CSF and TNF-α for 12 days differentiate into CD1a$^+$ DC (Caux, et al. (1996) *J Exp Med* 184:695–706). The expression of Langerin during such cultures was investigated. Langerin is expressed by a subset of CD1a$^+$ dendritic cells derived from cord blood CD34$^+$ HPC. Kinetics of CD1a and Langerin expression during culture of CD34$^+$ HPC in GM-CSF plus TNF-α was determined at various time points, cells were recovered and double-labeled using anti-CD1a-FITC and DCGM4 plus anti-mouse IgG-PE. The results are representative of 5 experiments.

No staining was detected at day 0 or day 6, indicating that CD34$^+$ HPC and their immediate progeny do not express Langerin. The antigen appeared at day 7, on a small subset of the CD1a$^+$ cells. Between day 7 to day 12, Langerin expression reached a maximum, staining between 15 to 35% of CD1a$^+$ cells. The dendritic nature of the Langerin-expressing cells in the cultures was confirmed on cytospin preparations of DCGM4$^+$ FACS-sorted cells.

Caux, et al. (1996) *J Exp Med* 184:695–706 have further shown that CD34$^+$ HPC differentiate along two independent pathways from distinct precursor subsets, identified by mutually exclusive expression of CD1a and CD14 at early time points during the culture (day 5–7). When such precursors were separated by FACS-sorting at day 6 and cultured with GM-CSF and TNF-α for 6 more days, Langerin was found mostly expressed on the CD1a-derived DC (40%) as compared to the CD14-derived DC (16%). The CD1a-derived DC have been shown to display features that are associated with Langerhans cells, including the presence of Birbeck granules.

Next, the in situ distribution of Langerin was examined by immunohistological analysis of various human tissues. Langerin is selectively expressed by LC-like DC. Immunohistological analysis of Langerin expression was made on sections of skin, tonsil and lung. Within the epidermis, Langerin was only found on LC, which also stained with anti-Lag and anti-CD1a antibodies. In skin, staining with mAb DCGM4, or mAb DCGM4 plus anti-Lag or anti-CD1a, showed positive Langerin expression by LC. In tonsil, the Langerin-positive cells were found in the epithelium (e.g., on follicular mantle B cells). A few cells were occasionally stained in the T cell areas, but never observed in germinal centers Langerin$^+$ cells were also notably present in lung epithelium. In lung, mAb TNF-α was determined at various time points, cells were recovered and double-labeled using anti-CD1a-FITC and DCGM4 plus anti-mouse IgG-PE. The results are representative of 5 experiments.

No staining was detected at day 0 or day 6, indicating that CD34$^+$ HPC and their immediate progeny do not express Langerin. The antigen appeared at day 7, on a small subset of the CD1a$^+$ cells. Between day 7 to day 12, Langerin expression reached a maximum, staining between 15 to 35% of CD1a$^+$ cells. The dendritic nature of the Langerin-expressing cells in the cultures was confirmed on cytospin preparations of DCGM4+FACS-sorted cells.

Caux, et al. (1996) *J Exp Med* 184:695–706 have further shown that CD34$^+$ HPC differentiate along two independent pathways from distinct precursor subsets, identified by mutually exclusive expression of CD1a and CD14 at early time points during the culture (day 5–7). When such precursors were separated by FACS-sorting at day 6 and cultured with GM-CSF and TNF-α for 6 more days, Langerin was found mostly expressed on the CD1a-derived DC (40%) as compared to the CD14-derived DC (16%). The CD1a-derived DC have been shown to display features that are associated with Langerhans cells, including the presence of Birbeck granules.

Next, the in situ distribution of Langerin was examined by immunohistological analysis of various human tissues. Langerin is selectively expressed by LC-like DC. Immunohistological analysis of Langerin expression was made on sections of skin, tonsil and lung. Within the epidermis, Langerin was only found on LC, which also stained with anti-Lag and anti-CD1a antibodies. In skin, staining with mAb DCGM4, or mAb DCGM4 plus anti-Lag or anti-CD1a, showed positive Langerin expression by LC. In tonsil, the Langerin-positive cells were found in the epithelium (e.g., on follicular mantle B cells). A few cells were occasionally stained in the T cell areas, but never observed in germinal centers Langerin$^+$ cells were also notably present in lung epithelium. In lung, mAb DCGM4 and counterstaining with hematoxylin showed LC-like Langerin$^+$ cells only in bronchiolar epithelium. The Langerin$^+$ DC showed dendritic morphology. No staining was detected with control mAbs. These results were representative of 5 experiments.

By contrast to CD34-derived DC, mAb DCGM4 did not react with DC obtained from peripheral blood monocytes cultured 6 days with a combination of GM-CSF and IL-4, thus, further confirming the restriction of Langerin expression. Likewise, Langerin was neither detected in ex-vivo purified DC isolated from peripheral blood, nor in germinal center DC isolated from tonsils.

Finally, mAb DCGM4 was analyzed for reactivity on a panel of different hematopoietic-derived cell types. Langerin was neither detected in ex-vivo isolated T lymphocytes, B lymphocytes, monocytes or granulocytes, nor in myeloid (HL60, KG1, U937, THP1) or lymphoid (Jurkat, JY, PREALP) cell lines.

Taken together, the above data suggest that Langerin expression is restricted to an immature DC compartment, and that it is subsequently lost upon DC maturation.

Example 12

Langerin Expression is Upregulated by TGF-β and Decreased Following CD40 Activation Since mAb DCGM4 was found to react selectively with LC-like immature DC, it was investigated whether factors that influence DC maturation would affect the expression levels of Langerin.

Studies in vitro and in vivo have shown that TGF-β plays an essential role in LC development. Therefore, the effect of TGF-β on Langerin expression by in vitro derived DC was evaluated.

To do so, cord blood CD34$^+$ HPC were cultured for 12 days in GM-CSF and TNF-α in absence or presence of TGF-β from day 7 to day 12. Subsequently, the DC were cultured with L-cells transfected with CD40L for 2 days. Cells were processed for staining without or after pretreatment with 0.1% saponin, using mAbs revealed by FITC-conjugated anti-mouse Ig. The results are representative of more than 5 experiments.

CD34-derived DC were supplemented with TGF-β for the last three days of culture (day 9–12). This resulted in strong upregulation of Langerin expression. In addition to increasing the proportion of Langerin$^+$ cells, TGF-β raised the mean number of surface-membrane molecules per cell (93×10$^3$ instead of 33×10$^3$ without TGF-β). The effect of TGF-β was predominantly exerted on the CD14-derived DC subset, normally devoid of Langerhans markers such as the Birbeck granule associated antigen Lag. Langerin expression is not restricted to the plasma membrane, but is also detected intracellulary following membrane permeabilization. Levels of intracellular Langerin were also markedly enhanced by TGF-β. It was also found that although TGF-β also increased the expression of the LC markers Lag and E-cadherin, Lag was never detected at the cell-surface.

Removal of TNF-α, a cytokine known to induce DC maturation, for the last three days of culture, upregulated Langerin expression whether in the presence or absence of TGF-β. In line with this result, a strong decrease in Langerin surface-membrane expression was found associated with an increase of HLA-DR following activation with CD40L, a signal which triggers the maturation of DC including upregulation of costimulatory molecules. Altogether, these results confirm that TGF-β which induces an LC phenotype, upregulates Langerin expression, whereas signals that trigger DC maturation decrease Langerin expression.

Example 13

Intracellular Langerin and Lag Co-Localize in Immature DC, but Dissociate Upon Activation A unique feature of Langerhans cells is the presence of intracytoplasmic Birbeck granules (BG). As Langerin was found to be selectively expressed in Langerhans-type DC, its relationship with Lag antigen was further examined. Thus, CD34-derived DC supplemented with TGF-β, and which contain a high proportion of BG$^+$ cells as detected by electron microscopy, were analyzed by double fluorescence staining and confocal microscopy. CD34-derived DC were supplemented with TGF-β from day 7 to day 9 of culture. Double-color confocal laser scanning microscopy was performed at day 9 and after two subsequent days of CD40L activation. Langerin-positive and Lag-positive vesicles were found co-localized in day 9 immature DC. After CD40L activation, Langerin$^+$Lag$^-$ staining was observed near the nucleus. No co-localization was detected between Langerin and HLA-DR or LAMP-1, irrespective of CD40L activation. Langerin and Lag were found to display a remarkable intracellular co-localization. Strikingly however, localization of the two markers segregated upon activation with CD40L. Thus, Langerin was found in the absence of Lag in close proximity to the nucleus, whereas a co-localized expression of the two markers only remained immediately beneath the surface membrane.

These results indicate that Langerin is distinct from Lag, and that Langerin is routed towards a deep cellular compartment during DC activation. Finally, Langerin was never found to co-localize with the lysosomal marker LAMP-1, nor with HLA-DR, irrespective of activation by CD40 crosslinking.

Example 14

Langerin is Associated with Endocytic Structures and Birbeck Granules

Since Langerin is expressed at the cell surface (as detected by FACS in the absence of membrane permeabilization) electron microscopy was performed on epidermal cell suspensions to analyze its precise distribution. Langerhans cells are easily recognizable in such suspensions, by their folded nuclei, lack of keratin filaments, lack of desmosomes and melanosomes, and the presence of characteristic BG.

An epidermal cell suspension was obtained as described above. mAbs were revealed by 5 nm gold-labeled goat anti-mouse IgG1. CD1a is homogeneously distributed at the cell surface, whereas Langerin is often associated with areas of membrane thickening. Cytomembrane sandwiching structures and coated pits were visualized upon staining with DCGM4 at 4° C. Upon incubation at 37° C., cytoplasmic gold particle-containing coated vesicles and Birbeck granules were seen. DCGM4 staining and gold particles were revealed on the luminal side of BG. These results were representative of 3 experiments on different skin samples.

Staining at 4° C. with DCGM4 and 5 nm gold particles confirmed that Langerin is clearly associated with the cell surface in LC, although at a lower density than CD1a (161.5±97.1 versus 1589.1±418.8 gold granules/100 $\mu$m membrane). In addition to single gold particles, a spontaneous clustering was observed with DCGM4, even though the antibody was ultracentrifuged. An isotype-matched control mouse IgG1 did not bind to the LC (1.3±3.4 granules/100 $\mu$m). No labeling of DCGM4 was observed on the keratinocytes or melanocytes present in the epidermal cell suspensions.

As compared to the rather homogeneous distribution of CD1a, Langerin was not randomly distributed at the cell surface, but was often associated with particular areas of membrane thickening. Furthermore, DCGM4 induced typical endocytic coated pits at the cell membrane at 4° C. The number of coated pits was significantly enhanced (an average 3.6 times) by DCGM4, as compared to staining with anti-CD1a or control mouse IgG1. Notably, the coated pits induced during DCGM4 staining contained gold particles. Furthermore, when cells were allowed to warm up before fixation, DCGM4 staining was observed inside coated vesicles already after 2 min. at 37° C. These data demonstrate that Langerin is associated with structures characteristic of early steps of receptor-mediated endocytosis.

Staining with DCGM4 at 4° C. also resulted in the formation of cytomembrane sandwiching structures at the cell surface. Consistently, following DCGM4 at 4° C., gold labeled BG were seen in continuity with the cell membrane, and found inside the cytoplasm when cells were warmed up to 37° C. for 2 min. The BG were labeled in their central striated lamella or in their bulb.

Taken together, these results indicate that Langerin is associated with endocytic structures and can also gain access to Birbeck granules from the cell membrane.

Example 15

Langerin Mediates Rapid Internalization in DC

To further examine the role of Langerin in endocytosis, we analyzed its capacity to internalize DCGM4 as a ligand.

CD34-derived DC supplemented with TGF-$\beta$ were labeled at 4° C. with mAbs and subsequent F(ab')$_2$ biotinylated secondary antibody. Cells were incubated at 37° C. for time periods indicated, and internalization measured as decreased cell-surface-bound antibody determined by FACS analysis using PE-conjugated streptavidin. MAb DCGM4 is rapidly internalized at 37° C., with similar kinetics as an anti-mannose-receptor mAb (positive control). In fixed cells, no decrease of cell-surface fluorescence was detected. Results were analyzed as the percentage decrease of mean fluorescence intensity (MFI), as compared to control samples kept at 4° C.

It was found that the antibody was very rapidly internalized by DC at 37° C., but not at 4° C. Approximately 75% of surface-membrane bound DCGM4 was internalized already within one minute at 37° C., with similar kinetics to that of anti-mannose-receptor mAb DCGM1, used as positive control for receptor-mediated endocytosis. In a representative experiment, the half-life ($t_{1/2}$) of DCGM4 at the cytomembrane was calculated to be 4.5 minutes at 37° C., with an internalization rate of k=15.3%/min. The rapid disappearance of mAb DCGM4 from the cell-surface was not due to antibody dissociation, as no decrease in fluorescence was observed in glutaraldehyde-fixed DC incubated at 37° C. Finally, Langerin did not display a mannose-type receptor specificity, as DCGM4 failed to inhibit uptake of Dextran-FITC at 37° C. and binding of the antibody was not inhibited by mannan at 4° C.

These results are in accordance with the above electron microscopy analysis and demonstrate that Langerin is implicated in a rapid endocytosis process by DC.

Example 16

Triggering of Cell-Surface Langerin Results in Birbeck Granule Formation

As triggering of cell surface Langerin resulted in the formation of CMS and the detection of gold-labeled BG as visualized by electron microscopy, the potential role of Langerin cell surface in BG formation was further investigated. An epidermal cell suspension was obtained as described above. Cells were incubated with an excess of mAb DCGM4 or anti-CD1a at 4° C., and processed immediately for electron microscopy, or left at room temperature for 5 min. before fixation. LC incubated with DCGM4 displayed a striking accumulation of Birbeck granules in the perinuclear region. The effect is predominantly observed at 4° C., as subsequent warming up results in vacuolization. Treatment with anti-CD1a mAb failed to induce significant changes in the LC cytoplasm, whether in cells kept at 4° C. or brought up to room temperature.

This treatment resulted in a considerable increase of densely packed BG in the LC cytoplasm, with a marked accumulation in the perinuclear region around the Golgi. The BG displayed an elongated, round, or irregularly-shaped expanded portion, in addition to their typical rod-shaped part. Moreover, the cytoplasm of DCGM4-treated LC was filled with numerous rounded or elongated vesicles.

When LC were warmed up to room temperature (5 min.) following incubation with excess DCGM4, increased fusion was observed between single and short rod-shaped BG and large vesicular components. Moreover, numerous vesicles of various sizes and shapes occupied a considerable volume of the LC cytoplasm.

In contrast to DCGM4, incubation of epidermal cell suspensions with an excess anti-CD1a mAb only led to the formation of some small vesicles but no other significant changes in the LC cytoplasm. Notably, no accumulation of perinuclear BG was observed, even when cells were allowed to warm up before fixation. Similarly, incubation with a control mouse IgG1 or with anti-E-cadherin mAb did not modify the BG granules.

Taken together, these data demonstrate that cell-surface Langerin actively participates in BG formation, resulting in their perinuclear accumulation.

Example 17

Langerin is a 40 kDa N-Glycosylated Protein

Immunoprecipitation with DCGM4 from DC extracts and, subsequent elution with SDS-PAGE sample buffer yielded a homogeneous band of 40–42 kDa molecular mass. SDS-PAGE analysis of immunopurified Langerin in non-reducing and reducing conditions was carried out. If DTT was omitted all along the purification steps, the profile was not modified on the gel, suggesting that Langerin is present at the cell membrane as a single chain or as an homodimer with non covalent association.

2-D analysis of immunopurified Langerin was conducted establishing the molecular mass of the molecule and indicating that Langerin had a pI of 5.2–5.5. Finally, a dot-blot analysis of Langerin using (1) creatinase from *E. coli* as non-glycosylated control, (2) transferrin as positive N-glycosylated control, (3) N-glycosidase, (4) Langerin, and (5) N-glycosidase-treated Langerin, demonstrated that Langerin is a glycoprotein, and that most of the carbohydrate constituents were removed by N-glycosylase treatment.

Example 18

Isolating a Nucleic Acid Encoding a Langerin

Numerous methods are available to isolate a gene encoding a purified protein, especially where antibodies which recognize the protein exist. One method is to determine methods for purification of the protein and subsequently to determine the peptide sequences. Given sufficient sequence information, and using redundant oligonucleotides, PCR or hybridization techniques will allow for isolation of genes encoding Langerin proteins.

Another alternative is to generate additional antibodies to Langerin proteins, which may be isolated by immunoaffinity methods using the DCGM4 antibodies. See above. These antibodies are applicable in "panning" techniques, such as described by Seed and Aruffo (1987) *Proc. Nat'l Acad. Sci. USA* 84:3365–3369. Phage expression techniques are also applicable to screen cDNA libraries derived from appropriate DC or T cell subpopulations enriched for Langerin expression. Glycosylation interference with antibody recognition will be generally less problematic in the phage selection systems. Cell sorting techniques on a mammalian expression library are applicable also.

Another method for screening an expression library is to use antibody to screen successive subpopulations of libraries. The following provides one method of screening using small populations of cells on slides stained by a specific labeling composition, e.g., an antibody.

For example, on day 0, precoat 2-chamber permanox slides with 1 ml per chamber of fibronectin, 10 ng/ml in PBS, for 30 min. at room temperature. Rinse once with PBS. Then plate COS cells at 2–3×10⁵ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µDNA in serum free DME. For each set, a positive control is prepared, e.g., of human IL-10-FLAG cDNA construct at 1 and 1/200 dilution, and a negative mock. Rinse cells with serum free DME. Add the DNA solution and incubate 5 h at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1M NaN₃ for 20 min. Cells are then washed with HBSS/saponin 1×. Soluble antibody, e.g., DCGM4, is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min., which closes cells. Then add Vector diaminobenzoic acid (DAB) for 5 to 10 min. Use 2 drops of buffer plus 4 drops DAB plus 2 drops of H₂O₂ per 5 ml of glass distilled water. Carefully remove chamber and rinse slide in water. Air dry for a few minutes, then add 1 drop of Crystal Mount and a cover slip. Bake for 5 min. at 85–90° C.

Alternatively, the Langerin proteins are used to affinity purify or sort out cells expressing the ligand. See, e.g., Sambrook, et al. (supra) or Ausubel, et al., (supra) both of which are incorporated herein by reference.

Example 19

Human Genomic Langerin

The genomic sequence (SEQ ID NO: 3) and the exon-intron organization of human Langerin has now been determined. The genomic sequence includes the Langerin cDNA sequence (SEQ ID NO: 1) as 6 exons separated by 5 introns. The nucleotide sequences of exons 1–6 are provided in SEQ ID NOS 4–9 respectively. This 10,663 nucleotide genomic sequence includes 3251 and 1808 nucleotides at the 5' and 3' ends of exons 1 and 6 respectively, and is predicted to include the sequence of the human Langerin promoter.

Exon 1 (SEQ ID NO: 4) corresponds to positions 3252–3371 of SEQ ID NO: 3. Exon 2 (SEQ ID NO: 5) corresponds to positions 3467–3583 of SEQ ID NO: 3. Exon 3 (SEQ ID NO: 6) corresponds to positions 5051–5425 of SEQ ID NO: 3. Exon 4 (SEQ ID NO: 7) corresponds to positions 6020–6171 of SEQ ID NO: 3. Exon 5 (SEQ ID NO: 8) corresponds to positions 7252–7370 of SEQ ID NO: 3. Exon 6 (SEQ ID NO: 9) corresponds to positions 7871–8855 of SEQ ID NO: 3.

Human Langerin is a 328 amino acid transmembrane type II Ca++ dependent lectin. Amino-acid translation of the 6 exons shows that exon 1 encodes the NH2-terminal portion of the intracellular domain (24 amino acids), while both the membrane-proximal portion of the intracellular domain (19 amino acids) and the entire transmembrane domain (20 amino acids) are encoded by exon 2. Exon 3 encodes the entire membrane-proximal non-carbohydrate recognition portion of the extracellular domain (125 amino acids). The extracellular carbohydrate-recognition domain (CRD) is encoded jointly by exons 4 (51 amino acids), 5 (39 amino acids), and the beginning of exon 6 (50 amino acids) the latter terminating the COOH-portion of the molecule. Notably, the CRD of Langerin shares the three exon structure of other type II transmembrane lectins including the Kuppfer cell receptors, rat hepatic lectin, and the CD23 low-affinity IgE receptor, with the coding sequences interrupted by introns at analogous positions.

The availability of the genomic Langerin sequence now allows for the identification of human Langerin promoter elements, expected to be situated within the 500–600 nucleotides 5' of the ATG initiation codon at position 48 of exon 1. By analogy, in the rat Kuppfer cell receptor, homologous to human Langerin, the transcription initiation site is situated 51 bases upstream from the ATG translation initiation codon. Two nucleotide sequences have been identified 5' to the start of transcription, that are candidates for regulation of gene expression. One is a 54-base tandomly repeated sequence from nucleotides −151 to −98 and −97 to −44, and the other is a heptanucleotide sequence (GAGGCAG) that is repeated 4 times in 380 bases 5' to the start site (G. W. Hoyle and R. L. Hill, J. Biol Chem, 1991, 266:1850–1857).

Human Langerin is specifically expressed in Langerhans cells, a subtype of immature dendritic cells specialized in capture and processing of antigen. Thus, it will be feasible to construct DNA sequences encoding antigens of choice for targeting selective expression in Langerhans cells under control of the Langerin promoter elements.

Human Langerin sequence enables the identification of the mouse homolog Langerin genomic sequence. This information will be key to the construction of mice deficient in the Langerin gene, to further explore the function of Langerin and of the Birbeck granules, the unique endocytic organelles of Langerhans cells that are induced by engagement of Langerin.

The human Langerin sequence also enables the sequencing of possible mutations in the Langerin gene in patients suffering from immunological disorders of unknown etiology.

Example 20

Chromosomal Mapping of Human Langerin

Chromosomal localization was performed by radiation hybrid (RH) mapping (D. R. Cox et al., Science, 1990, 250: 245–250), using the Stanford G3 Radiation Hybrid panel (Research Genetics, Inc., Huntsville, Ala.). Briefly, two oligonucleotides (U863 and L1180) used to amplify Langerin cDNA by PCR reaction were selected as they also amplified a stretch of human genomic DNA. PCR reactions were carried out with U863/L1180 on the Stanford G3 panel of 83 clones covering the human genome. PCR data were submitted to the Stanford Human Genome Center RHserver (LIENHYPERTEXTE mailto:rhserver@paxil.stanford.edu rhserver@paxil.stanford.edu) for mapping using the RHMAP statistical program (RHMAP).

Results from the RH Server indicated as closest matches the markers SHGC-58922 (LOD score: 8.67) and SHGC-12714 (LOD score 7.74). Both markers are located on chromosome 2, linked to the GDB locus D2S292 (SHGC source AFH203yb6†: SHGC-1610 microsatellite marker). Genes mapping near the D2S292 locus include†: transforming growth factor-alpha precursor (2 p13), dynactin (2 p13), gamma actin enteric smooth muscle form (2 p13), annexin IV (2 p13), MAD (2 p12–13), alpha-CP1, early growth response 4, nucleolysin TIA-1, protein tyrosine phosphatase P, protein kinase C substrate 80K-H, glutamine-fructose 6-phosphate transaminase, retinoic acid-responsive protein, RAB.1A, and pleckstrin. The results localize the gene of human Langerin to chromosome 2 p13, in the vicinity of the D2S292 locus.

The localization of human Langerin will permit to survey immunological genetic disorders for a potential association with the chromosome 2p13 region.

Example 21

Identification of Mouse Langerin

Using the nucleotide sequence of the human Langerin, a search was performed in the NCBI database. This permitted to identify two mouse ESTs (AA764540 and AA423304) displaying considerable homology to the human sequence. These ESTs were then used to extend the sequence, using RACE-PCR on a mouse lung cDNA library: The entire coding region, with the exception of the extremity of the 5' end was determined. Nine nucleotides completing the sequence were subsequently identified by sequencing a mouse cosmid clone. A contig of 1756 nucleotides was obtained and is shown in SEQ ID NO: 10.

An open-reading frame of 978 nucleotides was identified (positions 266–1243 in the contig of SEQ ID NO: 10), encoding a predicted transmembrane type II Ca++ dependent lectin of 326 amino acids (SEQ ID NO: 11). The mouse amino acid sequence presents considerable homology (66.6%) with human Langerin (alignment shown in Table 1), with conservation of the key structural features of the molecule (ie. intracytoplasmic proline-rich motif as potential signal transduction site, and extracellular carbohydrate-recognition domain (CRD) with an EPN motif as found in human Langerin and indicative of mannose-binding specificity). These data indicate that the above identified mouse molecule is the homolog of human Langerin.

The mouse Langerin protein has been succesfully expressed in mammalian cells (murine COP5 fibroblasts), which have been used for immunization of mice to produce monoclonal antibodies (mAbs). A number of mAbs recognizing mouse Langerin protein have been isolated 7 of these mAbs display crossreactivity on human Langerin. The epitopes recognized by the cross-reactive mAbs have all been mapped to the intracytoplasmic domain using truncated forms of recombinant human Langerin protein. This is consistent with the remarkably high conservation

TABLE 1

```
      M L V E E E A P D A H F T V D K Q N I S L W P R E P P P K S G L S L V L G K T L  Majority
                        10                  20                  30                  40
  1   M T V E K E A P D A H F T V D K Q N I S L W P R E P P P K S G P S L V P G K T P  hu Langerin aa
  1   M L - - E E A P E A H F T V D K Q N I S L W P R E P P P K Q D L S P V L R K P L  mouse langerin aa T V R A A L I C L A L V L V A S V V L Q A V L Y P R L M G T I L D V K S D A Q L  Majority
                        50                  60                  70                  80
 41   T V R A A L I C L T L V L V A S V L L Q A V L Y P R F M G T I S D V K T N V Q L  hu Langerin aa
 39   C I C V A F T C L A L V L V T S I V L Q A V F Y P R L M G K I L D V K S D A Q M  mouse langerin aa L K G R V D N I S T L G S D L K T E S G G V D A A G V Q I Q I V N T S L G R V R  Majority
                        90                 100                 110                 120
 81   L K G R V D N I S T L D S E I K K N S D G M E A A G V Q I Q M V N E S L G Y V R  hu Langerin aa
 79   L K G R V D N I S T L G S D L K T E R G R V D D A E V Q M Q I V N T T L K R V R  mouse langerin aa S Q I L S L E T S V E I A N A Q L L I L T R S W G E V S S L S A Q I P E L K S D  Majority
                       130                 140                 150                 160
121   S Q F L K L K T S V E K A N A Q I Q I L T R S W E E V S T L N A Q I P E L K S D  hu Langerin aa
119   S Q I L S L E T S M K I A N D Q L L I L T M S W G E V D S L S A K I P E L K R D  mouse langerin aa L D K A S A L N T K V Q G L Q G S L E N V S K L L K Q Q S D I L E V V A Q G W K  Majority
                       170                 180                 190                 200
161   L E K A S A L N T K I R A L Q G S L E N M S K L L K R Q N D I L Q V V S Q G W K  hu Langerin aa
159   L D K A S A L N T K V Q G L Q N S L E N V N K L L K Q Q S D I L E M V A R G W K  mouse langerin aa Y F S G N F Y Y F S L I P K T W Y S A E Q F C V S R N A H L T S V S S E S E Q E  Majority
                       210                 220                 230                 240
201   Y F K G N F Y Y F S L I P K T W Y S A E Q F C V S R N S H L T S V T S E S E Q E  hu Langerin aa
199   Y F S G N F Y Y F S R T P K T W Y S A E Q F C I S R K A H L T S V S S E S E Q K  mouse langerin aa F L Y K A A G G L I H N I G L T K A G S E G D W S W V D D T S F N K V Q S A R F  Majority
                       250                 260                 270                 280
241   F L Y K T A G G L I Y W I G L T K A G M E G D W S W V D D T P F N K V Q S A R F  hu Langerin aa
239   F L Y K A A D G I P H W I G L T K A G S E G D W Y W V D Q T S F N K E Q S R R F  mouse langerin aa W I P G E P N N A G N N E H C G N I K A S A L Q A W N D G P C D N T F L F I C K  Majority
                       290                 300                 310                 320
281   W I P G E P N N A G N N E H C G N I K A P S L Q A W N D A P C D K T F L F I C K  hu Langerin aa
279   W I P G E P N N A G N N E H C A N I R V S A L K C W N D G P C D N T F L F I C K  mouse langerin aa R P Y V Q S T E                                                                  Majority 321   R P Y V P S E P                                                                  hu Langerin aa
319   R P Y V Q T T E                                                                  mouse langerin aa
```

Table I shows the alignment between the amino acid sequences for human Langerin (SEQ ID NO: 2) and mouse Langerin (SEQ ID NO: 11). Table I also shows the Majority sequence (SEQ ID NO: 12).

Table I shows the alignment between the amino acid sequences for human Langerin (SEQ ID NO: 2) and mouse Langerin (SEQ ID NO: 11). Table I also shows the Majority sequence (SEQ ID NO: 12). in the cytoplasmic tail (first 30 residues) of human and mouse Langerin (see Table 1).

Availability of the sequence encoding mouse Langerin will permit the performance of studies (RT-PCR, Northerns, in situ hybridization) to determine the expression pattern of Langerin in various tissues. Furthermore, the current sequence can be extended to identify the genomic DNA in order to construct mice deficient in the Langerin gene. Such animals should be highly valuable to further understand the role of Langerin in the regulation of the immune response. MAbs directed against mouse Langerin will be useful to study expression of the protein in mouse tissues. Also, mAb can be injected in mice to analyze the impact of triggering Langerin on the dendritic cell system in vivo. These studies will be important to complement efforts to target antigen (ie. tumor antigens) to dendritic cells in vivo via their cell-surface Langerin with the aim of inducing protective anti-tumor immunity. Targeting experiments can, for instance, be performed by injecting mice (prior of after challenge with tumor) with mAb against mouse Langerin to which tumor antigen has been coupled chemically.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. SEQUENCE LISTING

What is claimed is:

1. A nucleic acid sequence which encodes a protein shown in SEQ ID NO: 2.

2. The nucleic acid sequence of claim 1 comprising the amino acid coding region shown in SEQ ID NO: 1.

3. A nucleic acid sequence comprising any one of SEQ ID NOs: 4–9.

4. An expression vector comprising the nucleic acid of claim 1.

5. A host cell comprising the vector of claim 4.

6. A process for producing a polypeptide comprising culturing the host cell of claim 5 under conditions in which the polypeptide is expressed.

* * * * *

SEQUENCE LISTING

```
<160> NUMBER OF SEQ ID NOS: 12

<210> SEQ ID NO 1
<211> LENGTH: 1547
<212> TYPE: DNA
<213> ORGANISM: Homo sapiens
<220> FEATURE:
<221> NAME/KEY: CDS
<222> LOCATION: (56)..(1039)

<400> SEQUENCE: 1
ctggaaaggg cagccagaag cacctgtgct cccaggataa gggtgagcac tcagg atg      58
                                                               Met
                                                               1 act gtg gag aag gag gcc cct gat gcg cac ttc act gtg gac aaa cag     106
Thr Val Glu Lys Glu Ala Pro Asp Ala His Phe Thr Val Asp Lys Gln
        5                   10                  15 aac atc tcc ctc tgg ccc cga gag cct cct ccc aag tcc ggt cca tct     154
Asn Ile Ser Leu Trp Pro Arg Glu Pro Pro Pro Lys Ser Gly Pro Ser
            20                  25                  30 ctg gtc ccg ggg aaa aca ccc aca gtc cgt gct gca tta atc tgc ctg     202
Leu Val Pro Gly Lys Thr Pro Thr Val Arg Ala Ala Leu Ile Cys Leu
        35                  40                  45 acg ctg gtc ctg gtc gcc tcc gtc ctg ctg cag gcc gtc ctt tat ccc     250
Thr Leu Val Leu Val Ala Ser Val Leu Leu Gln Ala Val Leu Tyr Pro
50                  55                  60                  65 cgg ttt atg ggc acc ata tca gat gta aag acc aat gtc cag ttg ctg     298
Arg Phe Met Gly Thr Ile Ser Asp Val Lys Thr Asn Val Gln Leu Leu
                70                  75                  80 aaa ggt cgt gtg gac aac atc agc acc ctg gat tct gaa att aaa aag     346
Lys Gly Arg Val Asp Asn Ile Ser Thr Leu Asp Ser Glu Ile Lys Lys
            85                  90                  95 aat agt gac ggc atg gag gca gct ggc gtt cag atc cag atg gtg aat     394
Asn Ser Asp Gly Met Glu Ala Ala Gly Val Gln Ile Gln Met Val Asn
        100                 105                 110 gag agc ctg ggt tat gtg cgt tct cag ttc ctg aag tta aaa acc agt     442
Glu Ser Leu Gly Tyr Val Arg Ser Gln Phe Leu Lys Leu Lys Thr Ser
    115                 120                 125 gtg gag aag gcc aac gca cag atc cag atc tta aca aga agt tgg gaa     490
Val Glu Lys Ala Asn Ala Gln Ile Gln Ile Leu Thr Arg Ser Trp Glu
130                 135                 140                 145 gaa gtc agt acc tta aat gcc caa atc cca gag tta aaa agt gat ttg     538
Glu Val Ser Thr Leu Asn Ala Gln Ile Pro Glu Leu Lys Ser Asp Leu
                150                 155                 160 gag aaa gcc agt gct tta aat aca aag atc cgg gca ctc cag ggc agc     586
Glu Lys Ala Ser Ala Leu Asn Thr Lys Ile Arg Ala Leu Gln Gly Ser
            165                 170                 175 ttg gag aat atg agc aag ttg ctc aaa cga caa aat gat att cta cag     634
Leu Glu Asn Met Ser Lys Leu Leu Lys Arg Gln Asn Asp Ile Leu Gln
        180                 185                 190 gtg gtt tct caa ggc tgg aag tac ttc aag ggg aac ttc tat tac ttt     682
Val Val Ser Gln Gly Trp Lys Tyr Phe Lys Gly Asn Phe Tyr Tyr Phe
    195                 200                 205
```

```
tct ctc att cca aag acc tgg tat agt gcc gag cag ttc tgt gtg tcc      730
Ser Leu Ile Pro Lys Thr Trp Tyr Ser Ala Glu Gln Phe Cys Val Ser
210             215                 220                 225 agg aat tca cac ctg acc tcg gtg acc tca gag agt gag cag gag ttt      778
Arg Asn Ser His Leu Thr Ser Val Thr Ser Glu Ser Glu Gln Glu Phe
            230                 235                 240 ctg tat aaa aca gcg ggg gga ctc atc tac tgg att ggc ctg act aaa      826
Leu Tyr Lys Thr Ala Gly Gly Leu Ile Tyr Trp Ile Gly Leu Thr Lys
        245                 250                 255 gca ggg atg gaa ggg gac tgg tcc tgg gtg gat gac acg cca ttc aac      874
Ala Gly Met Glu Gly Asp Trp Ser Trp Val Asp Asp Thr Pro Phe Asn
    260                 265                 270 aag gtc caa agt gcg agg ttc tgg att cca ggt gag ccc aac aat gct      922
Lys Val Gln Ser Ala Arg Phe Trp Ile Pro Gly Glu Pro Asn Asn Ala
275                 280                 285 ggg aac aat gaa cac tgt ggc aat ata aag gct ccc tca ctt cag gcc      970
Gly Asn Asn Glu His Cys Gly Asn Ile Lys Ala Pro Ser Leu Gln Ala
290                 295                 300                 305 tgg aat gat gcc cca tgt gac aaa acg ttt ctt ttc att tgt aag cga     1018
Trp Asn Asp Ala Pro Cys Asp Lys Thr Phe Leu Phe Ile Cys Lys Arg
                310                 315                 320 ccc tat gtc cca tca gaa ccg tgacaggaca ggctcccaag ctcactcttt        1069
Pro Tyr Val Pro Ser Glu Pro
                325 gagctccaac gcttgttaaa catgaggaaa tgcctctttc ttccccagac tccaggatga   1129 cttttgcacgt taattttttct tgcttcaaaa ttgtcccaca gtggcattct ggagtccgtc 1189 tgtcttggct ggaaattctc tgacgtcttg gaggcagctg gaatggaaag gagaattcag   1249 gttaaagtgg gaggggtggg tagagaggat ttagaagttc caattgccct gctaaggagg   1309 atcaagaccc gtaatccggc acaacaccct ggggttttcc actctttcag agaaacctca   1369 gcttcatcac atcaaagtta ctccagagca accaagcaat tctcctgata ttgtcatcca   1429 gggcttttct tggccaaacc ccctagaatt tccatgtctc tgcttagctg tgctggcagc   1489 tagcagctgg ctgtgtttgc agtgcaaata gctctgttct tggaaatcct gctcatgg    1547

<210> SEQ ID NO 2
<211> LENGTH: 328
<212> TYPE: PRT
<213> ORGANISM: Homo sapiens

<400> SEQUENCE: 2

Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
            20                  25                  30

Ser Leu Val Pro Gly Lys Thr Pro Thr Val Arg Ala Ala Leu Ile Cys
        35                  40                  45

Leu Thr Leu Val Leu Val Ala Ser Val Leu Gln Ala Val Leu Tyr
    50                  55                  60

Pro Arg Phe Met Gly Thr Ile Ser Asp Val Lys Thr Asn Val Gln Leu
65                  70                  75                  80

Leu Lys Gly Arg Val Asp Asn Ile Ser Thr Leu Asp Ser Glu Ile Lys
                85                  90                  95

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
```

```
                115                 120                 125
Ser Val Glu Lys Ala Asn Ala Gln Ile Gln Ile Leu Thr Arg Ser Trp
    130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
    210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
            260                 265                 270

Asn Lys Val Gln Ser Ala Arg Phe Trp Ile Pro Gly Glu Pro Asn Asn
        275                 280                 285

Ala Gly Asn Asn Glu His Cys Gly Asn Ile Lys Ala Pro Ser Leu Gln
    290                 295                 300

Ala Trp Asn Asp Ala Pro Cys Asp Lys Thr Phe Leu Phe Ile Cys Lys
305                 310                 315                 320

Arg Pro Tyr Val Pro Ser Glu Pro
                325

<210> SEQ ID NO 3
<211> LENGTH: 10663
<212> TYPE: DNA
<213> ORGANISM: Homo sapiens

<400> SEQUENCE: 3
tccctgtccc cactccgcaa tttggtgttc actctacttt cctccatgac ttgactgagg      60
gacttgggtg actcctccct ggagatgact cttggcactg ctggagcatt tcatacaacc     120
caggtctctg ttccagtctt gttgattaaa cccatggttc tcctccaagc ataaggctgg     180
gcccaaccat agtctcaacc agagaaaggg aaaaagtgac caagctgttt tcttcctcca     240
tccttatcca gagaaaatat tagaacccca ggaacacagg aagaggagaa actaaaaaaa     300
tgagcacaga cttcccgttc tcatcacagc ggtgattttt ttggtcacta ggtctggcca     360
gagttcctct tctgtttgga agagcagggc attgtctgag tgcccgggag aactgcccac     420
cttcctgact ggaaagtgtg gccaaggcac ctgcctgctt ctctgtcttt tctcctgcca     480
ggccaggtgc cagatagagc atccagaggt ttgcacagga gaggtgctca ggaaagacct     540
gtagatgagc atgataatag gaagatggct tctgactccc tccctctcca caaagtggga     600
aatgaaactt cctatggttt gggactttta catccacctc ctctgaaacc ccagaaggcc     660
cacagcccac ggattccatg cctttttgctc agcttcctca tgctggaaca gcctttcgcc     720
tagcggtagc tattctacct acctcagcct gcatttccat cacttggagt aaatgctccc     780
tgctccagcc ccttcctatg ccatgggcca gccgctaagg cttcctcatc ctttcctggg     840
accaatgaga gggcatctgg ggggctctat aaagtataac tcataccaca aaccagcaga     900
```

-continued

```
gaaaacccaa cttcctgacc gagcggaaat ggacaagaca cttcccaggc acactgtgtg      960
gcggcttctt tcccgcaaat gcctcaggag gagacatgga cccctgcaag gccccttcta     1020
ccagggtctt gagtaatttg gattcttctc tatccccagg cccagaaata ggacaggcta     1080
tggatgaagg gccaggagcc aggagcagaa gggcagagat gattctggag ttaggctggg     1140
tcccaagcat gagagtccag aagtggaaca ttctaatcct gtctaagccc tgatggaacc     1200
aaggctctgc aaccacacga gccacctgaa gagagtagga atcttcatgg acacccagag     1260
gcaggcagtg atgtggagcc aggccctcat attcgggact atcaaatgtt aaaatttaga     1320
gcagacagca ggcctggaag ttacagacag gctgggtagg gaagcgatgg gacagaacaa     1380
atgagacacc atctttgcta cccagtttcc ttcccagagc ttcccagtgt ggggtcctct     1440
ctgggttccc tcatccagtc cgagaagcca ctccagcctg aggcccggtt agctggagag     1500
agagcatcaa gggcctgtaa ctacaatgag ctgcacatag catgggctg agcgtgcagc      1560 cactatcctc ccaagtacca aggtggcag tagcccctga agcataggt agatatttcc       1620 ttggccctgt taacttaacc tctaatcctg gtccctgata caggctgtca tccagctcca    1680
ctggctcagc ctcagcaggc ccaggacagc tttcttttcc tgcggccaga gcttttgttc    1740
attcctgggt aaggagtaaa tcacacttcc ccttatgctt ttgcattgaa gatgaatgag    1800
aacttctgga gacagtggaa aaaagcagca gcttctagaa ggcagatccc aggcccaga    1860 ctgtgtaaat gtctgagtgg catgatcagc tatcaagtct ccaagtcact taccattcac    1920
acatccatcc atgcatcctc tatccatcca ttcatccatt cacccatcct ccaattatct    1980
ggaccaattt ccttcttttt tctttccttc cctccctctt tcctctcctc tttcctatat    2040
tccaagaaat atttgtctag agtctgccat gtgccaaatt tctcagattt ggcagacttc    2100
ttcaaagcat gagaagccgc ccaggagaaa atttagtcct tcattgagcc caaatcagct    2160
cttctgtgcc ctgagcttct tgcacatatg gaactctcta tttaggacta caaagaagga    2220
gagaggaggt gcggacagag agagaggaga gagaaacaga acgattccta gtctgaggtt    2280
gctgagcgcc cctactttt ttgaaaatct cacatggtgc aggaagcagg gaggagaacc     2340
caagtcttag gtttacactt tgaatctcca agttgcatat tataaaggga tattgtatca    2400
gccaagatgc attaataaca ggaagcagga tattctattg caatggttgc ctatttggta    2460
tctctgcttc caggcttctc cccaccagtc tgctcctcac caggatcaga gtgatgtttc    2520
tacagtgtcc ctgtccttgt ctctctcctg cctgaagtcc ttaattggcc ccatgtcacc    2580
cacaagccag aggtccagct ccttgacatg atcagaagga tcttcatcat cagacccag    2640 gtgcctcttc aaccccgtgt gcatcccctt cctgttggaa tgtatatttt acattccagc    2700
aatattgcaa ctatttacaa tttgccaagc actccatgct atcttatgct ccatcctttg    2760
gcatatgctt atcttctac tggatttttt tttttcccat tactccattt catatgcttc     2820
tttgaactgg gcatatttgt ctcttgtgct catcaccttg caatttattt gctcatgtct    2880
gtctttccta ccagactatg agctgcttgg tgcaaggact gcgagttatt catcactgtg    2940
gccctatgcc tggtagagca tcagtaccta gaaggcactc agcctgtatt tgtgggtga     3000 atggatgggt ggatggatga cgagagtctt acaagagaaa tgggataggt ttgggacaag    3060
atggttaatg tatccatgta acagacccc agagaagaca acaaatggcc tcttcctgaa     3120
agctcagact tctgaggatg ggagtaagcc agacaaggta tctagtcagg aatagggaag    3180
ttgggatgat atggtgacct gctgtgggac tgacttcctg tttcctctag ataagagccc    3240
ttggagagac aggcagccag aagcacctgt gctcccagga taagggtgag cactcaggat    3300
```

-continued

```
gactgtggag aaggaggccc ctgatgcgca cttcactgtg gacaaacaga acatctccct    3360
ctggccccga gcaagccaca tcgctgctga gaacctgctc cgtgttctgt gtgcaaacct    3420
gccctttgct gctccttcaa cacacatttt cttcttcttc caacagagcc tcctcccaag    3480
tccggtccat ctctggtccc ggggaaaaca cccacagtcc gtgctgcatt aatctgcctg    3540
acgctggtcc tggtcgcctc cgtcctgctg caggccgtcc tttgtaagtc ctcatgtttc    3600
atcgtctggg cttagcccct ctctgtgcca gccggctccc ttcagatcga gaccacttcc    3660
ctgctctccg ggtttctcct cctgtggctt tttcatttgt ctccttcctc ctctttccat    3720
gtgcagtaac aggctgtgct gcccccagta cggtgagctg atgctctttc cctcccaatt    3780
tctgggagat tattgggatt agcatttgca cattggtgct caaggataca gtctttgtcc    3840
tcaggaaaca ttgatctagt tttacatcct gtgctatttt ctccccgtcc acccccccacc    3900
aatctgagct ctgctccttg gatctagagc cttgtggaca gtccttgaca gtgcaatgtc    3960
tcctgaccct gtgaaggacc gagcctcatg tatcattggc cccagctcac cagatggaga    4020
gcctggccaa cgagccaaca gatctccatg actcagtccc ctctccccag gactcgttgg    4080
tgctgtcttc attctcctgt ccctgtgaag atcacatcta gggaggcttc ctgctcattt    4140
gatgttgcat ggtttatctt tcttcctttt ctggctctgt caggcttcat ggcctttgct    4200
gctggcagag ccttcttcct cctgccaggg ctccaggaag cagagcaaag ggacccaaga    4260
agctgttggg ttttttttttc tccctctgtg gcctcgggac atatttgggc ttagacttgt    4320
aggctctgag cagagtcccc cttgccccat cctagacccc tggcctctaa catcgcattt    4380
tcctcagggc tcgcctttga gcctcttggt ttatctttga tcctctctct ggtacccagg    4440
cctgggacct gagcagaatg tgaaagtggg tggggcaagg gaaggggaga acagttttg    4500
taatctcctc ttccatgttc tctggagaag ccacttccag attagtggct ggttcttccc    4560
atggtcacag aggggcccat ggacagatgt ggggagtgg tgctgtccta gcagatggcc    4620
actgcagggg tttctgaaaa cagagggatg gcaaccaagg ggtgggtct agggggaatc    4680
aagttctggg gacagtggtg gggctcatgg agggcaccct ttatcaaatg ttccctgaac    4740
actcagaaaa ttcaggaatg gtttctaact cctgcttctg cttgcctgtg aaatcttttc    4800
acagagagcc tgtgttttat caatctcccc attatctgta tccacctgtg ttcctggcac    4860
atggtaggtg cccattgcac gtttgttgta cgttaatgaa tgattggagg gttggggtgg    4920
cccattggac tgtcttggtt cttgggaag cttcagccta ttccttccct tcctttgatc    4980
aacctgacaa caccccccact cctgtccctg ggactcccct cagctgacct cctgactttc    5040
tcaatcccag atccccggtt tatgggcacc atatcagatg taaagaccaa tgtccagttg    5100
ctgaaaggtc gtgtggacaa catcagcacc ctggattctg aaattaaaaa gaatagtgac    5160
ggcatggagg cagctggcgt tcagatccag atggtgaatg agagcctggg ttatgtgcgt    5220
tctcagttcc tgaagttaaa aaccagtgtg gagaaggcca acgcacagat ccagatctta    5280
acaagaagtt gggaagaagt cagtaccta aatgcccaaa tcccagagtt aaaaagtgat    5340
ttggagaaag ccagtgcttt aaatacaaag atccgggcac tccagggcag cttggagaat    5400
atgagcaagt tgctcaaacg acaaagtaag tgactcagaa aattcatttg aagctgacca    5460
gtggcccatg ggatcttacc tgtcccagac ctgaggccat tgggctggtg ggttggggag    5520
gagagtgggg gcaaaagagg ggcagccatg ggctaggaag ttaaggagag agggcttgag    5580
gttggggagg acttagggc tgttaggaga aaagagacca gggtccagct agagctccca    5640
```

```
cacaaaagtg cagaatgtaa aagcattagg ggatgtccac cctggcccac acctagtcat    5700
ttcccatcaa gttcctttct agagtccagg ggctcagcca cttgtcatgg ccgatggagg    5760
gttgcttcct catcatgggg aagacactct ttgtccaacc tcttgcatta taacctctcc    5820
agtcccagag actctattag tctctgtctg actttcagga tttgaaagag tgtccctaat    5880
ctcctataca aggacccaag gacaccagcg cacagctcca tttgctgctg tctctgagac    5940
ctcattcaag tgcccccacc aagccagcat cccaagaaat caagaatacc agcgttcact    6000
tttacctctt gttctctaga tgatattcta caggtggttt ctcaaggctg gaagtacttc    6060 aagggggaact tctattactt ttctctcatt ccaaagacct ggtatagtgc cgagcagttc    6120
tgtgtgtcca ggaattcaca cctgacctcg gtgacctcag agagtgagca ggtgagtgct    6180
gtgcctatgg gctctgtgaa gggggcgtat gagcactggg ccagggagga tgggcaagat    6240
tatactgcgt gaacaaaaat ccccaaatat tgatgaccta atgaagaagg attggttctc    6300
agtagcatgt cgaataaggg ccggcaaggg ggctgtgctc actgtggcta ctcaaggacc    6360
caggcccaag gagtcttcat cttaatatgt ctccacaatt gctggggcag gaaaggggaa    6420
cttgacatat tgtgcaaagc ttctgcccag atttaacata cctcattttt gcttacattt    6480
cactagctta agttatgtta attaagttaa gtaagttatg cagtactcct ggattgggag    6540
gatcctggat tccagtactc ctggaacagg gcagagagga tctactttcc atgtgcccag    6600 aaaaaagaa atatttgtga acagccttaa tgattccaca tgactcaaga agtctcctgc    6660
ctggtgaggc agaaattggg caggcccttt tcatctggga ggtgggatag cagagcaggt    6720
cagagcctgg gctctggcgt agttctagag cctgaacctt gccatctaac tagtcctagc    6780
agcttgggtg gaatacccaa cttcactggg caaacttcac tggccctcac ttgatgaaac    6840
atgcatggtg atggcacctg cctcagagga aaggagagaa tgcatatgga cgactcagca    6900
cagtgccgta tgtggattca gggctcattt aattcaggta ttatcatatg aaccattctc    6960
ttgcggtccg tgctctggag ttcagctgag gccttcctgt gcttcagcac ctgcttcctg    7020
agtggcagaa aggcttgagt cctgagcttg ttagctgcag agcagggaca catcataatc    7080
tggaagatga atctgggct ctgggcaagg gcaggaagaa gcttgagagg ccagtttgtg    7140
cagcgcatct gtgggtcagg gctgtcactg agcgcaggtg aagaacaccc agagacagat    7200
gatcaagctc caagtgtggc cgcacctctg cttatcctgt ctttcctaca ggagtttctg    7260
tataaaacag cggggggact catctactgg attggcctga ctaaagcagg gatgaagggg    7320
gactggtcct gggtggatga cacgccattc aacaaggtcc aaagtgtgag gtaagcccct    7380
ggagccctcc gtgccagcct gactttcccc ggccatggcc agggcatgaa gggagtgggg    7440
gcgatgttcc ccatgagaca gggtttctga ttcttccctg tcttagagtg acaggaacat    7500
tgcaaccaag atcgagcaca accctgtcac caactggctg tggacctgag ccctccacgc    7560
cctctggggt ttggcaacaa ggccttctac ctggccagct tcagggatct tgtcatgagt    7620
ctaggtcttc acagtgtggg tttgtgtagg gacttgaaag tggtgggttg gtttggcctg    7680
gacttggggc atgtgaaagc ttagaggtcg aagtctcacc agtcccccttc ctctgaggct    7740 tgggtgcaga catttgctat gccattccct aggacaaaag cttgggttga gttaactcat    7800
ttcttcactg gaataagtt cttttttgatt ttccactttg taaatccatc ttttttccccg    7860 ctcttggtag gttctggatt ccaggtgagc ccaacaatgc tgggaacaat gaacactgtg    7920
gcaatataaa ggctccctca cttcaggcct ggaatgatgc cccatgtgac aaaacgtttc    7980
ttttcatttg taagcgaccc tatgtcccat cagaaccgtg acaggacagg ctcccaagct    8040
```

```
cactctttga gctccaacgc ttgttaaaca tgaggaaatg cctctttctt ccccagactc    8100
caggatgact ttgcacgtta attttttcttg cttcaaaatt gtcccacagt ggcattctgg   8160
agtccgtctg tcttggctgg aaattctctg acgtcttgga ggcagctgga atggaaagga    8220
gaattcaggt taaagtggga ggggtgggta gagaggattt agaagttcca attgccctgc    8280
taaggaggat caagacccgt aatccggcat aacaccctgg ggttttccac tctttcagag    8340
aaacctcagc ttcatcacat caaagttact ccagagcaac caagcaattc tcctgatatt    8400
gtcatccagg gcttttcttg gccaaacccc ctagaatttc catgtctctg cttagctgtg    8460
ctggcagcta gcagctggct gtgtttgcag tgcaaatagc tctgttcttg gaaatcctgc    8520
tcatggtatg tccccagtgg tttcttcatc cacatcatct aaagcctgaa cccgttcttc    8580
tctggttcaa gtcagtggct gacacggact tgtatctcct tcagagctcg gctggcaccc    8640
agcctccctt ctccttccac tcccttagta cactggagtg ccgagccctg ccttccaccc    8700
agcgtccatc cagcccctgt cctcacctct ccggcacctc ctcctccttc tgcatttcct    8760
atcttcctgt gtcttgtgca tgggaagcag ccttcagtgc cttcatgaat tcaccttcca    8820
gcttcctcag aataaaatgc tgcctgggtc aaggactcac tccaagtgca cttttttcatt  8880 tctggttgtc caggtgaata tgtgggaaag gcagtctcct ctggtggaca tgaagttcta   8940
gggtatcctc aggaaacatc tggggagtca aaaataacaa ggactgggga agttccagtc   9000
ctggaaatgc cacaaaatgt gaccagtact tatctctagt ttttattaaa gtagagcaag   9060
gtctccaatg tcacgatctt ggtgatcttt cttcttgttt actgcacaat cttctagtct   9120
atagctcaat tcccaagaac aagtctcagc aggttcccca ctcttcacag agacccagtt   9180
ccacaggcat cagttccaaa tcccaagtcc agtggctgaa gctggaatcc aggcagcagc   9240
caccacagag aggagaggag ggtggagtga gcacaggtct tcattaaggt cctcaggaaa   9300
agatgcttcc ttaaataact gtaaccagca gtgtgttgtt ctgggtgcaa atgggtcaca   9360
gctgagggca caggcttgta ttgtaagacc tgaaatacca cgtgctgctg tgacattta    9420 tgcctcacag ggccccaaag acctaaccct gagttccctg cctctcacca gatatatcct   9480
tgccctcggt ccccacctgg ctaatttcct atcatctgga ccagctgcat gccacccagt    9540
tttctactta atgggtttca cttctctgcc agcctgagaa actattcaaa caagccaatc    9600
acatcctcct acaggaatcc ggggcatctc atccttttat tactacaagg cctgcctccc    9660
acagccctgg ctggttcact ctgctcctga gggtgacccc atgtggccct gtgtggctta   9720
tgatatcttt ccccagtaga ctgtatttgt gactagtaaa ctgctgccag tctcacctgc    9780
acagtgtcaa atgtcttgtt ttggccatct tgtcctattt agagcagggg atccctccct    9840
caccaatgga ggaaatggga ggtgacaaga acaaggctgg tcgggatct ctggttggtt     9900 ttggcaaaga gatgagctgg gaaaatcaga ccatttctct gggaaagaat ttgaaccagg   9960
aaatagcaag aggatgaggc tgttaacaaa aggaagttga gctggaaggc actgagttaa   10020
gagaaaggct ggaggggccg tcacgtggca ttggaagaaa ctagcaatga gcagaagcta   10080
tgaggcaggg gaaagacatg aatacaggcc tggcatggtg gctcatgcct ataatcccag   10140
cactttggga ggctgaagtg ggtgggtcac ctgaggtcag gagttcgaga cagcctggcc   10200
aacatggtga aaccccatct ctactaaaaa tacaaaaatt agccgggcat ggtggtgggc   10260
acctgtaatt ccaactactt gggagactga ggcaggagaa ttgcttgaat ctgggaggca   10320
gaggttgcag tgagctgaga tcccaccact gcactccagc ctgggcaaca gggcaagact   10380
```

```
ttgtttcaaa aaaaagaag tgactgcaga ggattatagt tggcagagaa aagagaacgg      10440
ctcagaggag tcgcaatgga ggtcccggag ggcagcctga agggctccgg ctgctcccgt      10500
tcccagggct gcctcagatc ctcccagccc ttctgatcct cctggtttct gtgcatgggg      10560
accttacgag gctgtgctcc tgaccccaac cattgctttt tcttgaaact gaaagagcct      10620
gagtcagtga ggatgtgttt ttatctggag tctgtgcccc agc                       10663

<210> SEQ ID NO 4
<211> LENGTH: 120
<212> TYPE: DNA
<213> ORGANISM: Homo sapiens

<400> SEQUENCE: 4
ggcagccaga agcacctgtg ctcccaggat aagggtgagc actcaggatg actgtggaga      60
aggaggcccc tgatgcgcac ttcactgtgg acaaacagaa catctccctc tggccccgag      120

<210> SEQ ID NO 5
<211> LENGTH: 117
<212> TYPE: DNA
<213> ORGANISM: Homo sapiens

<400> SEQUENCE: 5
agcctcctcc caagtccggt ccatctctgg tcccggggaa acacccaca gtccgtgctg       60 cattaatctg cctgacgctg gtcctggtcg cctccgtcct gctgcaggcc gtcctttt       117

<210> SEQ ID NO 6
<211> LENGTH: 375
<212> TYPE: DNA
<213> ORGANISM: Homo sapiens

<400> SEQUENCE: 6
atccccggtt tatgggcacc atatcagatg taaagaccaa tgtccagttg ctgaaaggtc      60
gtgtggacaa catcagcacc ctggattctg aaattaaaaa gaatagtgac ggcatggagg      120
cagctggcgt tcagatccag atggtgaatg agagcctggg ttatgtgcgt tctcagttcc      180
tgaagttaaa aaccagtgtg gagaaggcca acgcacagat ccagatctta caagaagtt      240 gggaagaagt cagtacctta aatgcccaaa tcccagagtt aaaaagtgat ttggagaaag      300
ccagtgcttt aaatacaaag atccgggcac tccagggcag cttggagaat atgagcaagt      360
tgctcaaacg acaaa                                                      375

<210> SEQ ID NO 7
<211> LENGTH: 152
<212> TYPE: DNA
<213> ORGANISM: Homo sapiens

<400> SEQUENCE: 7
atgatattct acaggtggtt tctcaaggct ggaagtactt caaggggaac ttctattact      60
tttctctcat tccaaagacc tggtatagtg ccgagcagtt ctgtgtgtcc aggaattcac      120
acctgacctc ggtgacctca gagagtgagc ag                                   152

<210> SEQ ID NO 8
<211> LENGTH: 119
<212> TYPE: DNA
<213> ORGANISM: Homo sapiens

<400> SEQUENCE: 8
gagtttctgt ataaaacagc gggggactc atctactgga ttggcctgac taaagcaggg       60
```

```
atggaagggg actggtcctg ggtggatgac acgccattca acaaggtcca aagtgcgag    119
```

<210> SEQ ID NO 9
<211> LENGTH: 985
<212> TYPE: DNA
<213> ORGANISM: Homo sapiens

<400> SEQUENCE: 9

```
gttctggatt ccaggtgagc ccaacaatgc tgggaacaat gaacactgtg gcaatataaa     60
ggctccctca cttcaggcct ggaatgatgc cccatgtgac aaaacgtttc ttttcatttg    120
taagcgaccc tatgtcccat cagaaccgtg acaggacagg ctcccaagct cactctttga    180
gctccaacgc ttgttaaaca tgaggaaatg cctctttctt ccccagactc caggatgact    240
ttgcacgtta atttttcttg cttcaaaatt gtcccacagt ggcattctgg agtccgtctg    300
tcttggctgg aaattctctg acgtcttgga ggcagctgga atggaaagga gaattcaggt    360
taaagtggga ggggtgggta gagaggattt agaagttcca attgccctgc taaggaggat    420
caagacccgt aatccggcac aacaccctgg ggttttccac tctttcagag aaacctcagc    480
ttcatcacat caaagttact ccagagcaac caagcaattc tcctgatatt gtcatccagg    540
gcttttcttg gccaaacccc ctagaatttc catgtctctg cttagctgtg ctggcagcta    600
gcagctggct gtgtttgcag tgcaaatagc tctgttcttg gaaatcctgc tcatggtatg    660
tccccagtgg tttcttcatc cacatcatct aaagcctgaa cccgttcttc tctggttcaa    720
gtcagtggct gacacggact tgtatctcct tcagagctcg gctggcaccc agcctcccct    780
ctccttccac tcccttagta cactggagtg ccgagccctg ccttccaccc agcgtccatc    840
cagcccctgt cctcacctct ccggcacctc ctcctccttc tgcatttcct atcttcctgt    900
gtcttgtgca tgggaagcag ccttcagtgc cttcatgaat tcaccttcca gcttcctcag    960
aataaaatgc tgcctgggtc aagga                                         985
```

<210> SEQ ID NO 10
<211> LENGTH: 1756
<212> TYPE: DNA
<213> ORGANISM: Mus musculus
<220> FEATURE:
<221> NAME/KEY: CDS
<222> LOCATION: (266)..(1243)

<400> SEQUENCE: 10

```
ggcctctttg ctcgtttggt gtcttcagtt aagatgatta aaatgtctgt gtaccaggga     60
agtagtcagg tggcttcctc atcaaagccc aattcttagt caaaaggatg aagctgtggc    120
ctctgcctgg ctaatcgtct aagccaagaa ctgggaactt gggcatgaca aagtggcctg    180
cttttttggct catttcccgt ttcttttctgg atgaaaaggt ccttggggag acggatattc    240
```

```
agctttcct aagccagagg cagag atg ttg gag gag gct ccc gaa gcg cac     292
                            Met Leu Glu Glu Ala Pro Glu Ala His
                            1               5 ttc aca gtg gac aaa cag aac atc tct ctc tgg cct cga gag cct cct    340
Phe Thr Val Asp Lys Gln Asn Ile Ser Leu Trp Pro Arg Glu Pro Pro
10              15                  20                  25 ccc aag caa gat ctg tct cca gtt ctg agg aaa cct ctc tgt atc tgc    388
Pro Lys Gln Asp Leu Ser Pro Val Leu Arg Lys Pro Leu Cys Ile Cys
            30                  35                  40 gtg gcc ttc acc tgc ctg gca ttg gtg ctg gtc acc tcc att gtg ctt    436
Val Ala Phe Thr Cys Leu Ala Leu Val Leu Val Thr Ser Ile Val Leu
        45                  50                  55
```

```
cag gct gtt ttc tat cct agg ttg atg ggc aaa ata ttg gat gtg aag        484
Gln Ala Val Phe Tyr Pro Arg Leu Met Gly Lys Ile Leu Asp Val Lys
         60                  65                  70 agt gat gcc cag atg ttg aaa ggt cgt gtg gac aac atc agc acc ctg        532
Ser Asp Ala Gln Met Leu Lys Gly Arg Val Asp Asn Ile Ser Thr Leu
 75                  80                  85 ggt tct gat ctt aag act gaa aga ggt cgt gtg gac gat gct gag gtt        580
Gly Ser Asp Leu Lys Thr Glu Arg Gly Arg Val Asp Asp Ala Glu Val
 90                  95                 100                 105 cag atg cag ata gtg aac acc acc ctc aag agg gtg cgt tct cag atc        628
Gln Met Gln Ile Val Asn Thr Thr Leu Lys Arg Val Arg Ser Gln Ile
                110                 115                 120 ctg tct ttg gaa acc agc atg aag ata gcc aat gat cag ctc ctg ata        676
Leu Ser Leu Glu Thr Ser Met Lys Ile Ala Asn Asp Gln Leu Leu Ile
                125                 130                 135 tta aca atg agc tgg gga gag gtt gac agt ctc agt gcc aaa atc cca        724
Leu Thr Met Ser Trp Gly Glu Val Asp Ser Leu Ser Ala Lys Ile Pro
                140                 145                 150 gaa ctg aaa aga gat ctg gat aaa gcc agc gcc ttg aac aca aag gtc        772
Glu Leu Lys Arg Asp Leu Asp Lys Ala Ser Ala Leu Asn Thr Lys Val
                155                 160                 165 caa gga cta cag aac agc ttg gag aat gtc aac aag ctg ctc aaa caa        820
Gln Gly Leu Gln Asn Ser Leu Glu Asn Val Asn Lys Leu Leu Lys Gln
170                 175                 180                 185 cag agt gac att ctg gag atg gtg gct cga ggc tgg aag tat ttc tcg        868
Gln Ser Asp Ile Leu Glu Met Val Ala Arg Gly Trp Lys Tyr Phe Ser
                190                 195                 200 ggg aac ttc tat tac ttt tca cgc acc cca aag acc tgg tac agc gca        916
Gly Asn Phe Tyr Tyr Phe Ser Arg Thr Pro Lys Thr Trp Tyr Ser Ala
                205                 210                 215 gag cag ttc tgt att tct aga aaa gct cac ctg acc tca gtg tcc tca        964
Glu Gln Phe Cys Ile Ser Arg Lys Ala His Leu Thr Ser Val Ser Ser
                220                 225                 230 gaa tcg gaa caa aag ttt ctc tac aag gca gca gat gga att cca cac       1012
Glu Ser Glu Gln Lys Phe Leu Tyr Lys Ala Ala Asp Gly Ile Pro His
235                 240                 245 tgg att gga ctt acc aaa gca ggg agc gaa ggg gac tgg tac tgg gtg       1060
Trp Ile Gly Leu Thr Lys Ala Gly Ser Glu Gly Asp Trp Tyr Trp Val
250                 255                 260                 265 gac cag aca tca ttc aac aag gag caa agt agg agg ttc tgg att cca       1108
Asp Gln Thr Ser Phe Asn Lys Glu Gln Ser Arg Arg Phe Trp Ile Pro
                270                 275                 280 ggt gaa ccc aac aac gca ggg aac aac gag cac tgt gcc aat atc agg       1156
Gly Glu Pro Asn Asn Ala Gly Asn Asn Glu His Cys Ala Asn Ile Arg
                285                 290                 295 gtg tct gcc ctg aag tgc tgg aac gat ggt ccc tgt gac aat aca ttt       1204
Val Ser Ala Leu Lys Cys Trp Asn Asp Gly Pro Cys Asp Asn Thr Phe
                300                 305                 310 ctt ttc atc tgc aag agg ccc tac gtc caa aca act gaa tgacagatct        1253
Leu Phe Ile Cys Lys Arg Pro Tyr Val Gln Thr Thr Glu
315                 320                 325 ggcctgagct cggcatctgt ggggcaacag tgacctggct gaagagatgt ctctctccct     1313
gaggctccaa gattgctctg tacttacgtt tttttcttgc ttgaaaattg tcccaaacac     1373
agcctgtggt ctttctgtct tggctggcag ttctctgctc ctggaggcct tggaggagct    1433
tgggttaaac gggtgaggac ctgaaaaggg tgtagcagtc cttactgccc aggcgaggca    1493
ggtcagcaca ccaaacaggt tgtttagatt ttcctgatcc ttctcagaag ccttggctga   1553
```

-continued

```
ccatataaaa gctacattca aatatgacca gtatttgagg agacagacat gcccaaattt    1613
aaccatgata caatttatac aacatgtatt agaacacctc atggtatgtt caaaatagta    1673
aatatgttgt ttttatgtgc ctattgcaaa taaatgtaaa gacttaaaaa aaaaaaaaa     1733 aaaaaaaaaa aaaaaaaaaa aaa                                            1756
```

<210> SEQ ID NO 11
<211> LENGTH: 326
<212> TYPE: PRT
<213> ORGANISM: Mus musculus

<400> SEQUENCE: 11

```
Met Leu Glu Glu Ala Pro Glu Ala His Phe Thr Val Asp Lys Gln Asn
1               5                   10                  15

Ile Ser Leu Trp Pro Arg Glu Pro Pro Lys Gln Asp Leu Ser Pro
            20                  25                  30

Val Leu Arg Lys Pro Leu Cys Ile Cys Val Ala Phe Thr Cys Leu Ala
            35                  40                  45

Leu Val Leu Val Thr Ser Ile Val Leu Gln Ala Val Phe Tyr Pro Arg
    50                  55                  60

Leu Met Gly Lys Ile Leu Asp Val Lys Ser Asp Ala Gln Met Leu Lys
65                  70                  75                  80

Gly Arg Val Asp Asn Ile Ser Thr Leu Gly Ser Asp Leu Lys Thr Glu
                85                  90                  95

Arg Gly Arg Val Asp Asp Ala Glu Val Gln Met Gln Ile Val Asn Thr
            100                 105                 110

Thr Leu Lys Arg Val Arg Ser Gln Ile Leu Ser Leu Glu Thr Ser Met
        115                 120                 125

Lys Ile Ala Asn Asp Gln Leu Leu Ile Leu Thr Met Ser Trp Gly Glu
    130                 135                 140

Val Asp Ser Leu Ser Ala Lys Ile Pro Glu Leu Lys Arg Asp Leu Asp
145                 150                 155                 160

Lys Ala Ser Ala Leu Asn Thr Lys Val Gln Gly Leu Gln Asn Ser Leu
                165                 170                 175

Glu Asn Val Asn Lys Leu Leu Lys Gln Gln Ser Asp Ile Leu Glu Met
            180                 185                 190

Val Ala Arg Gly Trp Lys Tyr Phe Ser Gly Asn Phe Tyr Tyr Phe Ser
        195                 200                 205

Arg Thr Pro Lys Thr Trp Tyr Ser Ala Glu Gln Phe Cys Ile Ser Arg
    210                 215                 220

Lys Ala His Leu Thr Ser Val Ser Ser Glu Ser Glu Gln Lys Phe Leu
225                 230                 235                 240

Tyr Lys Ala Ala Asp Gly Ile Pro His Trp Ile Gly Leu Thr Lys Ala
                245                 250                 255

Gly Ser Glu Gly Asp Trp Tyr Trp Val Asp Gln Thr Ser Phe Asn Lys
            260                 265                 270

Glu Gln Ser Arg Arg Phe Trp Ile Pro Gly Glu Pro Asn Asn Ala Gly
        275                 280                 285

Asn Asn Glu His Cys Ala Asn Ile Arg Val Ser Ala Leu Lys Cys Trp
    290                 295                 300

Asn Asp Gly Pro Cys Asp Asn Thr Phe Leu Phe Ile Cys Lys Arg Pro
305                 310                 315                 320

Tyr Val Gln Thr Thr Glu
                325
```

```
<210> SEQ ID NO 12
<211> LENGTH: 328
<212> TYPE: PRT
<213> ORGANISM: Artificial
<220> FEATURE:
<223> OTHER INFORMATION: majority sequence between human and mouse
      Langerin

<400> SEQUENCE: 12

Met Leu Val Glu Glu Ala Pro Asp Ala His Phe Thr Val Asp Lys
1               5                   10                  15

Gln Asn Ile Ser Leu Trp Pro Arg Glu Pro Pro Lys Ser Gly Leu
            20                  25                  30

Ser Leu Val Leu Gly Lys Thr Leu Thr Val Arg Ala Ala Leu Ile Cys
            35                  40                  45

Leu Ala Leu Val Leu Val Ala Ser Val Val Leu Gln Ala Val Leu Tyr
        50                  55                  60

Pro Arg Leu Met Gly Thr Ile Leu Asp Val Lys Ser Asp Ala Gln Leu
65                      70                  75                  80

Leu Lys Gly Arg Val Asp Asn Ile Ser Thr Leu Gly Ser Asp Leu Lys
                85                  90                  95

Thr Glu Ser Gly Gly Val Asp Ala Ala Gly Val Gln Ile Gln Ile Val
            100                 105                 110

Asn Thr Ser Leu Gly Arg Val Arg Ser Gln Ile Leu Ser Leu Glu Thr
        115                 120                 125

Ser Val Glu Ile Ala Asn Ala Gln Leu Leu Ile Leu Thr Arg Ser Trp
130                 135                 140

Gly Glu Val Ser Ser Leu Ser Ala Gln Ile Pro Glu Leu Lys Ser Asp
145                 150                 155                 160

Leu Asp Lys Ala Ser Ala Leu Asn Thr Lys Val Gln Gly Leu Gln Gly
                165                 170                 175

Ser Leu Glu Asn Val Ser Lys Leu Leu Lys Gln Gln Ser Asp Ile Leu
            180                 185                 190

Glu Val Val Ala Gln Gly Trp Lys Tyr Phe Ser Gly Asn Phe Tyr Tyr
        195                 200                 205

Phe Ser Leu Ile Pro Lys Thr Trp Tyr Ser Ala Glu Gln Phe Cys Val
210                 215                 220

Ser Arg Asn Ala His Leu Thr Ser Val Ser Ser Glu Ser Glu Gln Glu
225                 230                 235                 240

Phe Leu Tyr Lys Ala Ala Gly Gly Leu Ile His Trp Ile Gly Leu Thr
                245                 250                 255

Lys Ala Gly Ser Glu Gly Asp Trp Ser Trp Val Asp Asp Thr Ser Phe
            260                 265                 270

Asn Lys Val Gln Ser Ala Arg Phe Trp Ile Pro Gly Glu Pro Asn Asn
        275                 280                 285

Ala Gly Asn Asn Glu His Cys Gly Asn Ile Lys Ala Ser Ala Leu Gln
    290                 295                 300

Ala Trp Asn Asp Gly Pro Cys Asp Asn Thr Phe Leu Phe Ile Cys Lys
305                 310                 315                 320

Arg Pro Tyr Val Gln Ser Thr Glu
                325
```